(12) United States Patent
Barrett et al.

(10) Patent No.: US 7,160,915 B2
(45) Date of Patent: Jan. 9, 2007

(54) N-METHYL-SUBSTITUTED BENZAMIDAZOLES

(75) Inventors: Stephen Douglas Barrett, Hartland, MI (US); Cathlin Marie Flamme, Lawrenceville, NJ (US); Michael David Kaufman, Ypsilanti, MI (US); Jared Bruce John Milbank, Dexter, MI (US); Haile Tecle, Ann Arbor, MI (US); Joseph Scott Warmus, Ann Arbor, MI (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 97 days.

(21) Appl. No.: 10/897,464

(22) Filed: Jul. 22, 2004

(65) Prior Publication Data

US 2005/0026970 A1 Feb. 3, 2005

Related U.S. Application Data

(60) Provisional application No. 60/490,012, filed on Jul. 24, 2003.

(51) Int. Cl.
*A61K 31/4184* (2006.01)
*C07D 235/22* (2006.01)
*C07D 235/06* (2006.01)

(52) U.S. Cl. ............... 514/395; 514/394; 548/309.7; 548/309.4; 548/307.4; 548/310.4

(58) Field of Classification Search ........... 548/309.7, 548/309.4, 307.4, 310.4; 514/395, 394
See application file for complete search history.

(56) References Cited

U.S. PATENT DOCUMENTS

| 5,155,110 A | 10/1992 | Connor et al. |
| 5,525,625 A | 6/1996 | Bridges et al. |
| 6,310,060 B1 | 10/2001 | Barrett et al. |
| 6,469,004 B1 | 10/2002 | Barrett et al. |
| 2004/0043388 A1 | 3/2004 | Come et al. |
| 2004/0116710 A1* | 6/2004 | Wallace et al. ............ 548/113 |
| 2005/0143438 A1 | 6/2005 | Wallace et al. |
| 2006/0106225 A1 | 5/2006 | Wallace et al. |

FOREIGN PATENT DOCUMENTS

| WO | WO 98/37881 | 9/1998 |
| WO | WO 99/01426 | 1/1999 |
| WO | WO 00/35436 | 6/2000 |
| WO | WO 00/42022 | 7/2000 |
| WO | WO 200042022 A1 * | 7/2000 |
| WO | WO 01/05390 | 1/2001 |
| WO | WO01/05392 | 1/2001 |
| WO | WO 200105390 A2 * | 1/2001 |
| WO | WO03/077855 | 9/2003 |
| WO | WO03/077914 | 9/2003 |

OTHER PUBLICATIONS

Bekemeier, H. et al., Structure-Activity Relationship in Nonsteroidal Antiinflammatory Agents, Including Qsar in Fenamate Derivatives, *Agents and Actions Supplements*, 1982, 8, 17-34.
Duesbery, N. et al., "MEK Wars, A New Front in the Battle Against Cancer," *Nature Medicine*, 1999, 5:7, 736-737.
Duncia, J. et al., "MEK Inhibitors: The Chemistry and Biological Activity of U0126, Its Analog, and Cyclization Products," *Bioorganic & Medicinal Chemistry Letters*, 1998, 8, 2839-2844.
Ru-Rong, J. et al., "Nociceptive-Specific Activation of ERK in Spinal Neurons Contributes to Pain Hypersensitivity," *Nature Nueroscience*, 1999, 2:12, 1114-1119.

* cited by examiner

*Primary Examiner*—Joseph K. McKane
*Assistant Examiner*—Michael Barker
(74) *Attorney, Agent, or Firm*—Bryan C. Zielinski; Galina M. Yakovleva

(57) ABSTRACT

The present invention relates to N-methyl-substituted benzamidazole derivatives of formula (I):

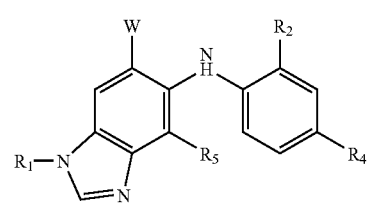

as defined in the specification; pharmaceutical compositions and methods of use thereof.

36 Claims, No Drawings

N-METHYL-SUBSTITUTED BENZAMIDAZOLES

FIELD OF THE INVENTION

This application claims the benefit of U.S. Provisional Application Ser. No. 60/490,012, filed Jul. 24, 2003.

The present invention relates to N-methyl-substituted benzamidazole derivatives, pharmaceutical compositions and methods of use thereof.

BACKGROUND OF THE INVENTION

MAPK/ERK Kinase ("MEK") enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates the MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative $Raf_{-1}$ protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to $Raf_{-1}$ and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

It has been found that the compounds of the present invention are inhibitors of MEK and are useful in the treatment of a variety of proliferative disease states, such as conditions related to the hyperactivity of MEK, as well as diseases modulated by the MEK cascade.

SUMMARY OF THE INVENTION

The present invention provides a compound of Formula

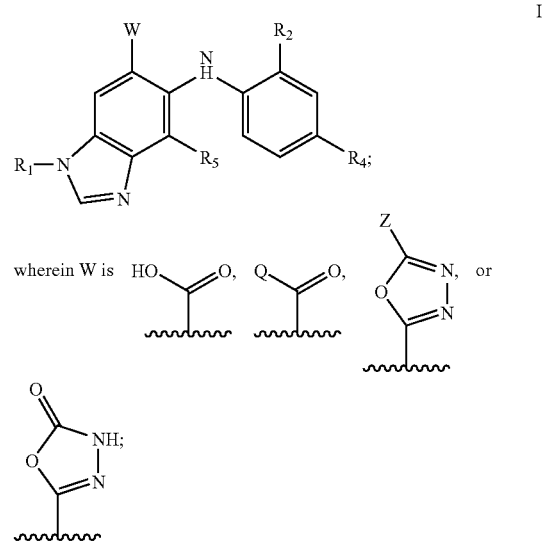

Q is —O—$R_3$, —$NH_2$, —NH[($CH_2$)$_k$$CH_3$], or —NH[O($CH_2$)$_k$$CH_3$], wherein the —$NH_2$ is optionally substituted with 1 and 2 substituents independently selected from methyl and —$NR_9R_{9a}$, and the —($CH_2$)$_k$$CH_3$ moieties of the —NH[($CH_2$)$_k$$CH_3$], and —NH[O ($CH_2$)$_k$ $CH_3$] groups are optionally substituted with 1 and 3 substituents independently selected from —OH, —$NR_9R_{9a}$, $C_{1-6}$ alkyl, and $C_3$–$C_{12}$cycloalkyl;

Z is —$NH_2$, —NH[($CH_2$)$_k$$CH_3$], or —NH[O($CH_2$)$_k$$CH_3$], wherein the —$NH_2$ is optionally substituted with 1 and 2 substituents independently selected from methyl and —$NR_9R_{9a}$; and the —($CH_2$)$_k$$CH_3$ moieties of the —NH [($CH_2$)$_k$$CH_3$], and —NH[O($CH_2$)$_k$$CH_3$] groups are optonally substituted with 1 and 3 substituents independently selected from —OH and —$NR_9R_{9a}$;

$R_1$ is hydrogen, $C_{1-6}$ alkyl, $C_{2-6}$ alkenyl, $C_{2-6}$ alkynyl, $C_3$–$C_{12}$cycloalkyl, —($CR_{10}R_{11}$)$_q$($C_6$–$C_{10}$ aryl), or —($CR_{10}R_{11}$)$_q$(4–10 membered heterocyclic); wherein said $R_1$ is optionally substituted with 1 to 3 substituents selected from the group consisting of —COOH, —COOR$_{14}$, —COR$_9$, —(CR$_{10}$R$_{11}$)$_q$(C$_6$–C$_{10}$ aryl), —(CR$_{10}$R$_{11}$)$_q$(4–10 membered heterocyclic), —SO$_2$R$_{11}$, —SO$_2$NR$_{12}$R$_{13}$, —OH, —OR$_{14}$, cyano, halo, —NR$_9$R$_{9a}$, and —NR$_9$CO(R$_{11}$);

R$_2$ is hydrogen, chlorine, fluorine or methyl;

R$_3$ is C$_{1-6}$ alkyl;

R$_4$ is bromine, chlorine, fluorine, iodine, C$_{1-6}$ alkyl, C$_{2-4}$ alkenyl, C$_{2-6}$ alkynyl, C$_{3-6}$ cycloalkyl, —(CH$_2$)—C$_{3-6}$ cycloalkyl, cyano, —O—(C$_{1-4}$ alkyl), —S—(C$_{1-2}$ alkyl), —SOCH$_3$, —SO$_2$CH$_3$, —SO$_2$NR$_6$R$_7$, —C≡C—(CH$_2$)$_n$NH$_2$, —C≡C—(CH$_2$)$_n$NHCH$_3$, —C≡C—(CH$_2$)$_n$N(CH$_3$)$_2$, —C≡C—CH$_2$OCH$_3$, —C=C(CH$_2$)$_n$OH, —C=C—(CH$_2$)$_n$NH$_2$, —CHCHCH$_2$OCH$_3$, —CHCH—(CH$_2$)$_n$NHCH$_3$, —CHCH—(CH$_2$)$_n$N(CH$_3$)$_2$, —(CH$_2$)$_p$CO$_2$R$_6$, —C(O)C$_{1-3}$ alkyl, C(O)NHCH$_3$, —(CH$_2$)$_m$NH$_2$, —(CH$_2$)$_m$NHCH$_3$, —(CH$_2$)$_m$N(CH$_3$)$_2$, —(CH$_2$)$_m$OR$_6$ —CH$_2$S(CH$_2$)t(CH$_3$), —(CH$_2$)$_p$CF$_3$, —C≡CCF$_3$, —CH=CHCF$_3$, —CH$_2$CHCF$_2$, —CH=CF$_2$, —(CF$_2$)$_v$CF$_3$, —CH$_2$(CF$_2$)$_v$CF$_3$, —(CH$_2$)$_t$CF(CF$_3$)$_2$, —CH(CF$_3$)$_2$, —CF$_2$CF(CF$_3$)$_2$, or —C(CF$_3$)$_3$, wherein the C$_{1-6}$ alkyl and C$_{2-6}$ alkynyl are optionally substituted with 1 and 3 substituents independently selected from —OH and C$_{1-6}$ alkyl;

R$_5$ is hydrogen or fluorine;

R$_6$ and R$_7$ are each independently hydrogen, methyl, or ethyl;

R$_9$ and R$_{9a}$ are each independently hydrogen or C$_{1-6}$ alkyl;

each R$_{10}$, R$_{11}$, R$_{12}$, and R$_{13}$ are C$_{1-6}$ alkyl or C$_{1-6}$ alkoxy;

R$_{14}$ is C$_{1-6}$ alkyl optionally optionally substituted with 1 to 3 substituents selected from the group consisting of —(CR$_{10}$R$_{11}$)$_q$(C$_6$–C$_{10}$ aryl), —(CR$_{10}$R$_{11}$)$_q$(4–10 membered heterocyclic);

k is 0 to 3;

m is 1 to 4;

n is 1 to 2;

p is 0 to 2;

t is 0 to 1;

v is 1 to 5;

q is o to 5:

and pharmaceutically acceptable salts thereof.

An embodiment of the present invention provide compounds of formula (I); wherein W is —CO—Q.

Additionally, the present invention also provides compounds of formula (I); wherein W is —CO—OH.

Additionally, the present invention also provides compounds of formula (I); wherein W is —CO—Q; wherein Q is —O—R$_3$, —NH$_2$, —NHR$_{10}$, —NR$_{10}$R$_{11}$, wherein the —NH$_2$ is optionally substituted with 1 and 2 substituents independently selected from methyl and amino, and the —O—R$_3$, R$_{10}$, and R$_{11}$ moieties are optionally substituted with 1 and 3 substituents independently selected from —OH, C$_{1-6}$ alkyl, and C$_{3-6}$ cycloalkyl.

Additionally provided by the present invention are compounds of Formula (I), wherein W is —CO—Q; wherein Q is —OCH$_2$CH$_3$, —NH$_2$, —NH[(CH$_2$)$_2$OH] or —NH[O(CH$_2$)$_2$OH].

Additionally provided by the present invention are compounds of Formula (I), wherein W is —CO—Q; wherein Q is —NH$_2$ or —NH[O(CH$_2$)$_2$OH].

The present invention also provides compounds of Formula I wherein R$_1$ is C$_{1-6}$ alkyl, wherein the C$_{1-6}$ alkyl is optionally substituted with 1 and 2 substituents independently selected from —OH, —COOH, and —COOR$_{14}$.

The present invention also provides compounds of Formula I wherein R$_1$ is methyl optionally substituted with a moiety selected from the group consisting of —COOH and —COOCH$_3$.

The present invention also provides compounds of Formula I wherein R$_1$ is methyl substituted with —COOH.

The present invention also provides compounds of Formula I wherein R$_2$ is fluorine or methyl.

The present invention also provides compounds of Formula I wherein R$_2$ is fluorine.

The present invention also provides compounds of Formula I wherein R$_4$ is iodine, C$_{1-3}$ alkyl, C$_{2-4}$ alkenyl, C$_{2-3}$ alkynyl, or —S—CH$_3$.

The present invention also provides compounds of Formula I wherein R$_4$ is iodine.

The present invention also provides compounds of Formula I wherein R$_4$ is ethyl, ethenyl, acetylene or —S—CH$_3$.

The present invention also provides compounds of Formula I wherein R$_4$ is iodine, ethyl, or acetylene.

The present invention also provides compounds of Formula I wherein R$_5$ is fluorine.

The present invention also provides compounds of Formula I, which is selected from the group consisting of:

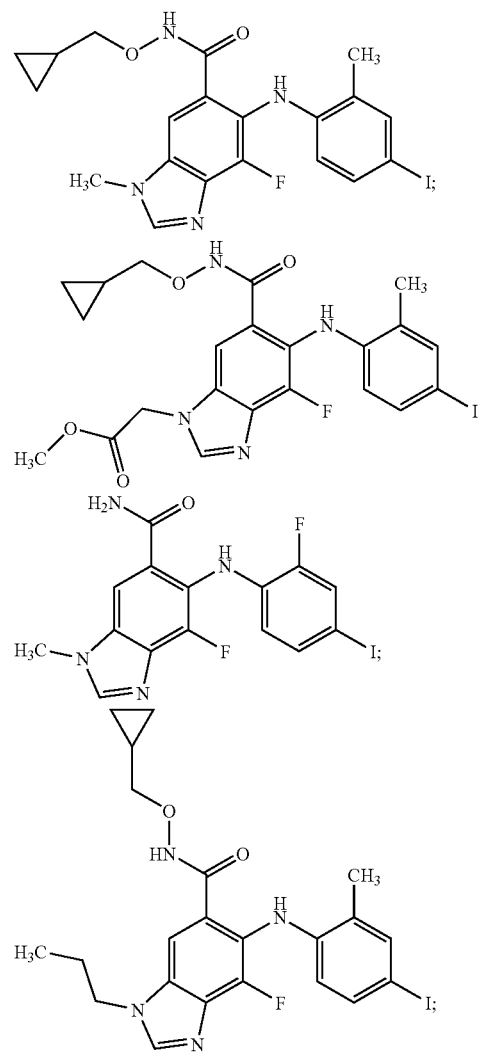

-continued

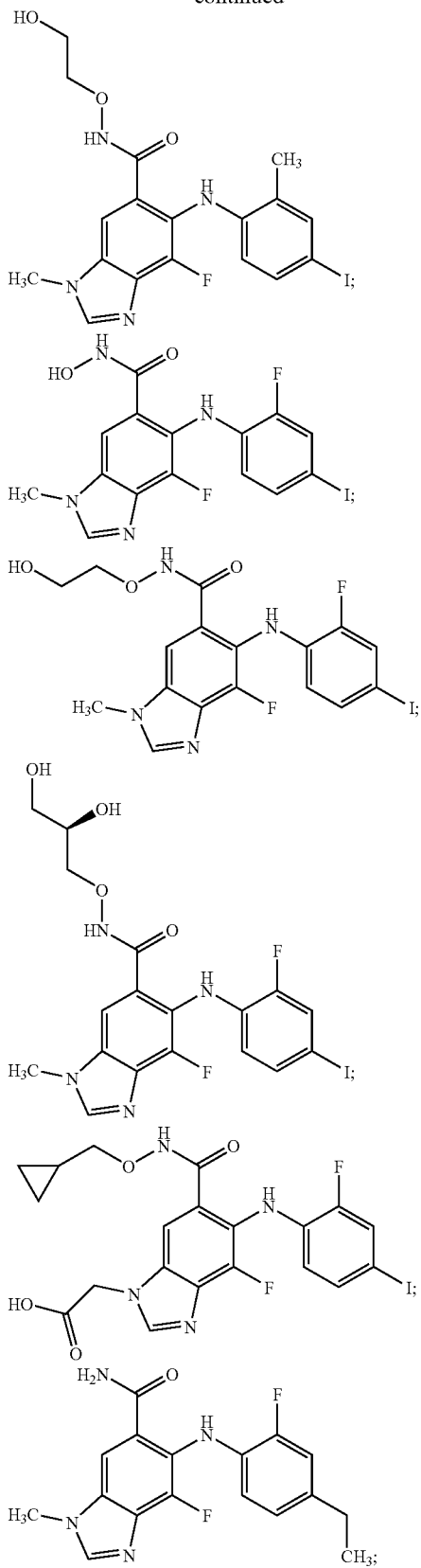

and the pharmaceutically acceptable salts thereof.

The present invention also provides a method of preparing a compound or a salt of formula (I):

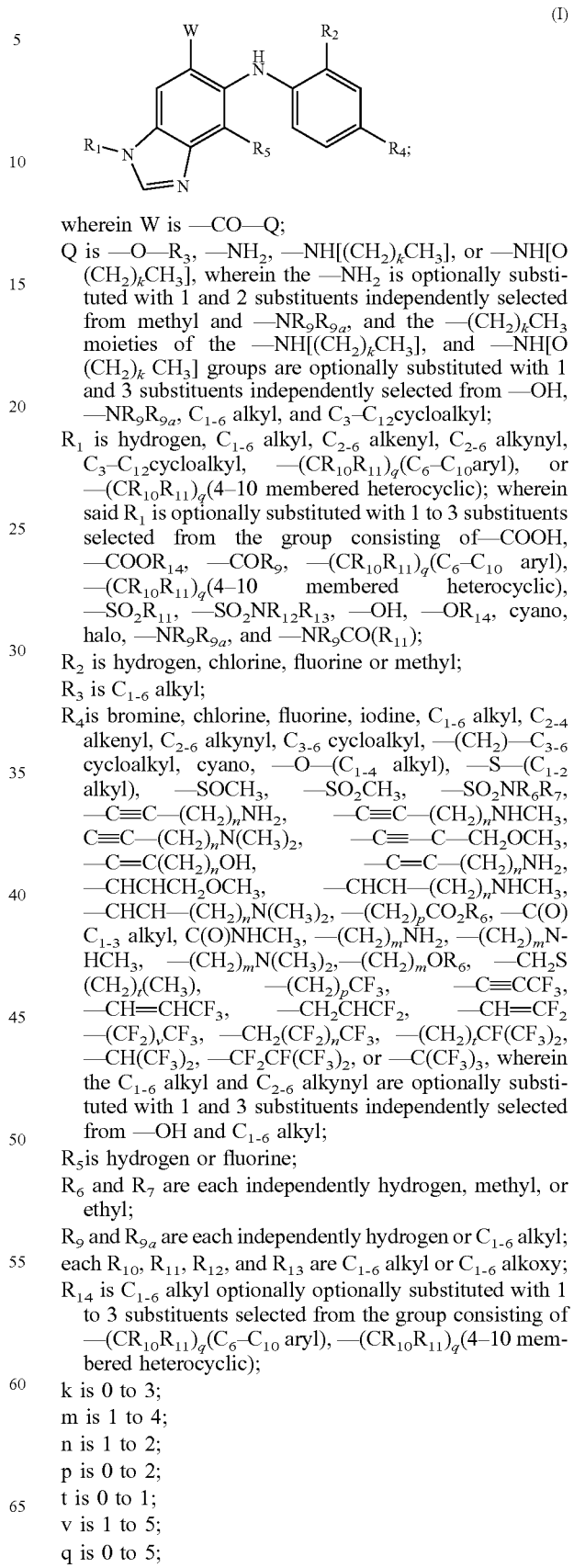

wherein W is —CO—Q;

Q is —O—$R_3$, —$NH_2$, —NH[$(CH_2)_kCH_3$], or —NH[O$(CH_2)_kCH_3$], wherein the —$NH_2$ is optionally substituted with 1 and 2 substituents independently selected from methyl and —$NR_9R_{9a}$, and the —$(CH_2)_kCH_3$ moieties of the —NH[$(CH_2)_kCH_3$], and —NH[O$(CH_2)_k CH_3$] groups are optionally substituted with 1 and 3 substituents independently selected from —OH, —$NR_9R_{9a}$, $C_{1-6}$ alkyl, and $C_3$–$C_{12}$cycloalkyl;

$R_1$ is hydrogen, $C_{1-6}$ alkyl, $C_{2-6}$ alkenyl, $C_{2-6}$ alkynyl, $C_3$–$C_{12}$cycloalkyl, —$(CR_{10}R_{11})_q(C_6$–$C_{10}$aryl), or —$(CR_{10}R_{11})_q$(4–10 membered heterocyclic); wherein said $R_1$ is optionally substituted with 1 to 3 substituents selected from the group consisting of—COOH, —$COOR_{14}$, —$COR_9$, —$(CR_{10}R_{11})_q(C_6$–$C_{10}$ aryl), —$(CR_{10}R_{11})_q$(4–10 membered heterocyclic), —$SO_2R_{11}$, —$SO_2NR_{12}R_{13}$, —OH, —$OR_{14}$, cyano, halo, —$NR_9R_{9a}$, and —$NR_9CO(R_{11})$;

$R_2$ is hydrogen, chlorine, fluorine or methyl;

$R_3$ is $C_{1-6}$ alkyl;

$R_4$ is bromine, chlorine, fluorine, iodine, $C_{1-6}$ alkyl, $C_{2-4}$ alkenyl, $C_{2-6}$ alkynyl, $C_{3-6}$ cycloalkyl, —$(CH_2)$—$C_{3-6}$ cycloalkyl, cyano, —O—($C_{1-4}$ alkyl), —S—($C_{1-2}$ alkyl), —$SOCH_3$, —$SO_2CH_3$, —$SO_2NR_6R_7$, —C≡C—$(CH_2)_nNH_2$, —C≡C—$(CH_2)_nNHCH_3$, C≡C—$(CH_2)_nN(CH_3)_2$, —C≡—C—$CH_2OCH_3$, —C≡C$(CH_2)_nOH$, —C≡C—$(CH_2)_nNH_2$, —$CHCHCH_2OCH_3$, —CHCH—$(CH_2)_nNHCH_3$, —CHCH—$(CH_2)_nN(CH_3)_2$, —$(CH_2)_pCO_2R_6$, —C(O)$C_{1-3}$ alkyl, $C(O)NHCH_3$, —$(CH_2)_mNH_2$, —$(CH_2)_mN$-$HCH_3$, —$(CH_2)_mN(CH_3)_2$,—$(CH_2)_mOR_6$, —$CH_2S$ $(CH_2)_t(CH_3)$, —$(CH_2)_pCF_3$, —C≡$CCF_3$, —CH═$CHCF_3$, —$CH_2CHCF_2$, —CH═$CF_2$ —$(CF_2)_vCF_3$, —$CH_2(CF_2)_nCF_3$, —$(CH_2)_tCF(CF_3)_2$, —$CH(CF_3)_2$, —$CF_2CF(CF_3)_2$, or —$C(CF_3)_3$, wherein the $C_{1-6}$ alkyl and $C_{2-6}$ alkynyl are optionally substituted with 1 and 3 substituents independently selected from —OH and $C_{1-6}$ alkyl;

$R_5$ is hydrogen or fluorine;

$R_6$ and $R_7$ are each independently hydrogen, methyl, or ethyl;

$R_9$ and $R_{9a}$ are each independently hydrogen or $C_{1-6}$ alkyl;

each $R_{10}$, $R_{11}$, $R_{12}$, and $R_{13}$ are $C_{1-6}$ alkyl or $C_{1-6}$ alkoxy;

$R_{14}$ is $C_{1-6}$ alkyl optionally optionally substituted with 1 to 3 substituents selected from the group consisting of —$(CR_{10}R_{11})_q(C_6$–$C_{10}$ aryl), —$(CR_{10}R_{11})_q$(4–10 membered heterocyclic);

k is 0 to 3;
m is 1 to 4;
n is 1 to 2;
p is 0 to 2;
t is 0 to 1;
v is 1 to 5;
q is 0 to 5;

comprising the step of:

(a) treating a compound of formula (II):

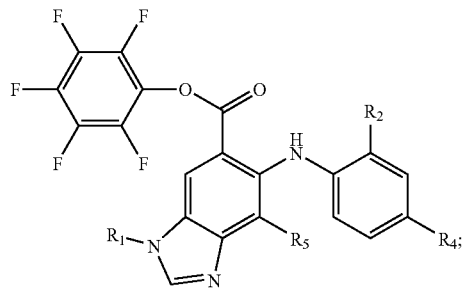

wherein $R_1$, $R_2$, $R_4$, and $R_5$ are as described above;

with a compound of formula (III):

$$Q\text{—}H \qquad (III);$$

wherein Q is as described above; in a solvent, to form said compound of formula (I).

In another embodiment, the present invention provides a method of preparing a compound or a salt of formula (I), wherein W is —CO—Q; and Q is —O—$R_3$, —$NH_2$, —$NHR_{10}$, —$NR_{10}R_{11}$, wherein the —$NH_2$ is optionally substituted with 1 and 2 substituents independently selected from methyl and amino, and the —O—$R_3$, $R_{10}$, and $R_{11}$ moieties are optionally substituted with 1 and 3 substituents independently selected from —OH, $C_{1-6}$ alkyl, and $C_{3-6}$ cycloalkyl.

In another embodiment, the present invention provides a method of preparing a compound or a salt of formula (I), wherein W is —CO—Q; and Q is —$NR_{10}R_{11}$ (i.e., compounds of formula Ia):

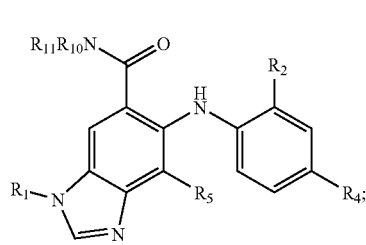

wherein $R_1$ is hydrogen, $C_{1-6}$ alkyl, $C_{2-6}$ alkenyl, $C_{2-6}$ alkynyl, $C_3$–$C_{12}$cycloalkyl, —$(CR_{10}R_{11})_q$($C_6$–$C_{10}$ aryl), or —$(CR_{10}R_{11})_q$(4–10 membered heterocyclic); wherein said $R_1$ is optionally substituted with 1 to 3 substituents selected from the group consisting of —COOH, —$COOR_{14}$, —$COR_9$, —$(CR_{10}R_{11})_q$($C_6$–$C_{10}$ aryl), —$(CR_{10}R_{11})_q$(4–10 membered heterocyclic), —$SO_2R_{11}$, —$SO_2NR_{12}R_{13}$, —OH, —$OR_{14}$, cyano, halo, —$NR_9R_{9a}$, and —$NR_9CO(R_{11})$;

$R_2$ is hydrogen, chlorine, fluorine or methyl;

$R_4$ is bromine, chlorine, fluorine, iodine, $C_{1-6}$ alkyl, $C_{2-4}$ alkenyl, $C_{2-6}$ alkynyl, $C_{3-6}$ cycloalkyl, —$(CH_2)$—$C_{3-6}$ cycloalkyl, cyano, —O—($C_{1-4}$ alkyl), —S—($C_{1-2}$ alkyl), —$SOCH_3$, —$SO_2CH_3$, —$SO_2NR_6R_7$, —C≡C—$(CH_2)_n NH_2$, —C≡C—$(CH_2)_n NHCH_3$, —C≡C—$(CH_2)_n N(CH_3)_2$, —C≡C—$CH_2OCH_3$, —C≡C$(CH_2)_n OH$, —C≡C—$(CH_2)_n NH_2$, —CHCH$CH_2OCH_3$, —CHCH—$(CH_2)_n NHCH_3$, —CHCH—$(CH_2)_n N(CH_3)_2$, —$(CH_2)_p CO_2R_6$, —C(O)$C_{1-3}$ alkyl, C(O)$NHCH_3$, —$(CH_2)_m NH_2$, —$(CH_2)_m N$-$HCH_3$, —$(CH_2)_m N(CH_3)_2$ —$(CH_2)_m OR_6$, —$CH_2S$$(CH_2)_t(CH_3)$—$(CH_2)_p CF_3$, —C≡C—$CF_3$, —CH═CHCF$_3$, —$CH_2CHCF_2$, —CH═$CF_2$, —$(CF_2)_v\ CF_3$, —$CH_2(CF_2)_n CF_3$, —$(CH_2)_t CF(CF_3)_2$, —$CH(CF_3)_2$, —$CF_2CF(CF_3)_2$, or —$C(CF_3)_3$, wherein the $C_{1-6}$ alkyl and $C_{2-6}$ alkynyl are optionally substituted with 1 and 3 substituents independently selected from —OH and $C_{1-6}$ alkyl;

$R_5$ is hydrogen or fluorine;

$R_6$ and $R_7$ are each independently hydrogen, methyl, or ethyl;

$R_9$ and $R_{9a}$ are each independently hydrogen or $C_{1-6}$ alkyl; each $R_{10}$, $R_{11}$, $R_{12}$, and $R_{13}$ are $C_{1-6}$ alkyl or $C_{1-6}$ alkoxy;

$R_{14}$ is $C_{1-6}$ alkyl optionally optionally substituted with 1 to 3 substituents selected from the group consisting of —$(CR_{10}R_{11})_q$($C_6$–$C_{10}$ aryl), —$(CR_{10}R_{11})_q$(4–10 membered heterocyclic);

comprising the step of:

(a) treating a compound of formula (IIa):

wherein $R_1$, $R_2$, $R_4$, and $R_5$ are as described above;

with a compound of formula $$R_{10}R_{11}NH \qquad (IIIa);$$

wherein $R_{10}$ and $R_{11}$ are as described above; in a solvent, to form said compound of formula (Ia).

In another embodiment, the present invention provides a method of preparing said compound or a salt of formula (I) said method further comprising the step of preparing said compound of formula (II); comprising:

(b) treating a compound of formula (IV):

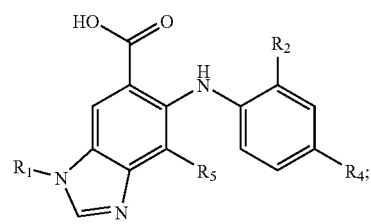

wherein $R_1$, $R_2$, $R_4$, and $R_5$ are as described above;

with a compound of formula $C_6F_5OH$ in the presence of a coupling agent in a solvent.

In one embodiment, the coupling agent is DCC.

In another embodiment, the present invention provides a method of preparing said compound or a salt of formula (II), said method further comprising the step of preparing said compound of formula (IV); comprising:

(c) treating a compound of formula (V):

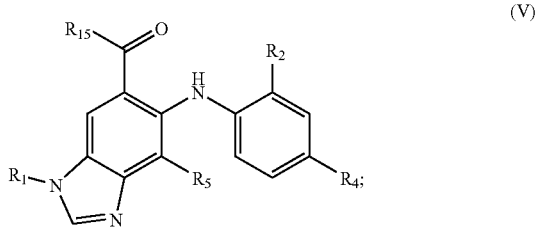

wherein $R_1$, $R_2$, $R_4$, and $R_5$ are as described above; and
$R_{15}$ is —O—$R_3$, —$NH_2$, —NH[$(CH_2)_k CH_3$], or —NH[O$(CH_2)_k CH_3$], wherein the —$NH_2$ is optionally substituted with 1 and 2 substituents independently selected from methyl and —$NR_9 R_{9a}$, and the —$(CH_2)_k CH_3$ moieties of the —NH[$(CH_2)_k CH_3$], and —NH[O$(CH_2)_k CH_3$] groups are optionally substituted with 1 and 3 substituents independently selected from —OH, —$NR_9 R_{9a}$, $C_{1-6}$ alkyl, and $C_3$–$C_{12}$cycloalkyl;
wherein $R_3$, $R_9$, $R_{9a}$, and k are as described above;
with a hydrolyzing agent in a solvent.

In one embodiment, the hydrolizing agent is potassium trimethyl silanote. In a preferred embodiment, in said compound of formula (V), $R_{15}$ is —O—$R_3$, wherein $R_3$ is $C_{1-6}$ alkyl; such as methyl.

In another embodiment, said method further comprising the step of preparing said compound of formula (V); comprising:

(d) treating a compound of formula (VI):

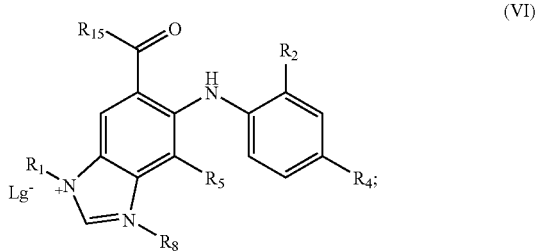

wherein $R_1$, $R_2$, $R_4$, and $R_5$ are as described above;
$R_8$ is selected from the group consisting of $C_{1-6}$ alkyl, $C_{2-6}$ alkenyl, $C_{2-6}$ alkynyl, $C_3$–$C_{12}$cycloalkyl, —$(CR_{10}R_{11})_q$$(C_6$–$C_{10}$ aryl), —$(CR_{10}R_{11})_q$(4–10 membered heterocyclic) and —$OSiR_{11}R_{12}R_{13}$; wherein said $R_8$ is optionally substituted with 1 to 3 substituents selected from the group consisting of —$(CR_{10}R_{11})_q$$(C_6$–$C_{10}$ aryl), —$(CR_{10}R_{11})_q$(4–10 membered heterocyclic), —$SO_2R_{11}$, —$SO_2NR_{12}R_{13}$ —OH, —$OR_{14}$, cyano, —$SiR_{11}R_{12}R_{13}$, halo, —$NH_2$, and —NHCO($R_{11}$); Lg is a leaving group selected from the group consisting of halo, sulfate esters, sulfonate esters, tetrafluoroborate and hexafluorophosphate;
each q is 0 to 5;
each $R_{10}$, $R_{11}$, $R_{12}$, and $R_{13}$ are $C_{1-6}$ alkyl or $C_{1-6}$ alkoxy;

$R_{14}$ is $C_{1-6}$ alkyl optionally optionally substituted with 1 to 3 substituents selected from the group consisting of —$(CR_{10}R_{11})_q$$(C_6$–$C_{10}$ aryl), —$(CR_{10}R_{11})_q$(4–10 membered heterocyclic);
$R_{15}$ is as described above;
with a deprotecting agent in a solvent.

In one embodiment, $R_8$ is allyl or 4-methoxybenzyl. In another embodiment, $R_8$ is —$OSiR_{11}R_{12}R_{13}$. In another embodiment, Lg is triflate, mesylate, tosylate, tetrafluoroborate or hexafluorophosphate. In a preferred embodiment, in said compound of formula (VI), $R_{15}$ is —O—$R_3$, wherein $R_3$ is $C_{1-6}$ alkyl; such as methyl.

In another embodiment, the present invention provides a method of preparing said compound or a salt of formula (IV) further comprising the step of preparing said compound of formula (VI); comprising:

(e) treating a compound of formula (VII):

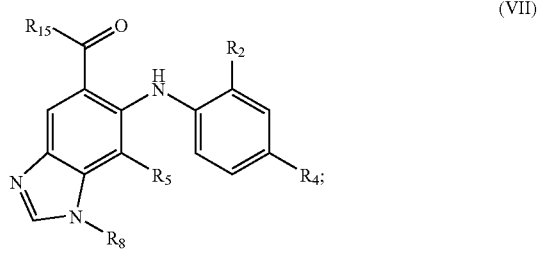

wherein $R_2$, $R_4$, $R_5$, $R_8$, and $R_{15}$ are as described above;
with a suitable alkylating agent; in a solvent.

In one embodiment, said suitable alkylating agent is $C_{1-6}$alkyl tosylate, such as methyl tosylate; or $C_{1-6}$alkyl triflate, such as methyl triflate.

In another embodiment, said suitable alkylating agent is $C_{1-6}$alkyl halide; such as methyl iodide.

In another embodiment, said suitable alkylating agent is trimethyloxonium tetrafluoroborate.

In a preferred embodiment, in said compound of formula (VII), $R_{15}$ is —O—$R_3$, wherein $R_3$ is $C_{1-6}$ alkyl; such as methyl.

In another embodiment, the present invention provides a method of preparing said compound or a salt of formula (VI), further comprising the step of preparing said compound of formula (VII); comprising:

(f) treating a compound of formula (VIII):

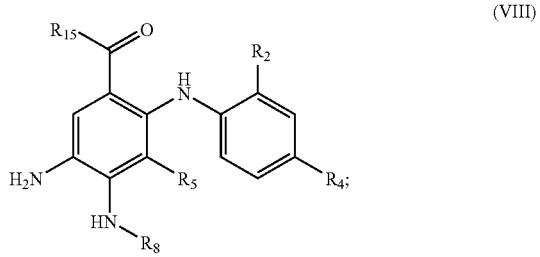

wherein $R_2$, $R_4$, $R_5$, $R_8$, and $R_{15}$ are as described above;
with a cyclocondensation agent; in a solvent.
Said cyclocondensation agents include formic acid, trimethylorthoformate, formamidine acetate, or ethyl formate. In a preferred embodiment, in said compound of formula (VIII), $R_{15}$ is —O—$R_3$, wherein $R_3$ is $C_{1-6}$ alkyl; such as methyl.

In another embodiment, the present invention provides a method of preparing said compound or a salt of formula (VII), further comprising the step of preparing said compound of formula (VIII); comprising:

(g) treating a compound of formula (IX):

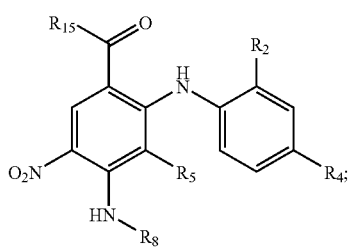

(IX)

wherein $R_2$, $R_4$, $R_5$, $R_8$, and $R_{15}$ are as described above;
with a reducing agent; in a solvent.

In a preferred embodiment, in said compound of formula (IX), $R_{15}$ is —O—$R_3$, wherein $R_3$ is $C_{1-6}$ alkyl; such as methyl.

In another embodiment, the present invention provides a method of preparing said compound or a salt of formula (VIII), further comprising the step of preparing said compound of formula (IX); comprising:

(h) treating a compound of formula (X):

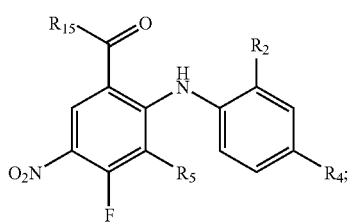

(X)

wherein $R_2$, $R_4$, $R_5$, and $R_{15}$ are as described above;
with a compound of formula $R_8$—$NH_2$, wherein $R_8$ is as described above; in a solvent.

In one embodiment, said compound of formula $R_8$—$NH_2$ is 2-hydroxyethylamine or 4-methoxybenzylamine. In a preferred embodiment, in said compound of formula (X), $R_{15}$ is —O—$R_3$, wherein $R_3$ is $C_{1-6}$ alkyl; such as methyl.

In another embodiment, the present invention provides a method of preparing said compound or a salt of formula (IX), further comprising the step of preparing said compound of formula (X); comprising:

(i) treating a compound of formula (XI):

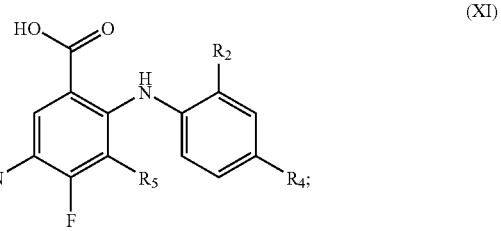

(XI)

wherein $R_2$, $R_4$, and $R_5$ are as described above;
with a suitable esterificating agent or a suitable amidating agent; in a solvent.

In one embodiment, a suitable esterificating agent includes a combination of a halogenating agent, such as $SOCl_2$, and a suitable alcohol, such as H—O—$R_3$. In another embodiment, a suitable esterificating agent includes a combination of a catalytic acid, such as catalytic HCl, and a suitable alcohol, such as H—O—$R_3$. In another embodiment, a suitable amidating agent includes includes a combination of a halogenating agent, such as $SOCl_2$, and a suitable amine, such as —$NH_2$, —$NH[(CH_2)_kCH_3]$, or —$NH[O(CH_2)_kCH_3]$.

In another embodiment, the present invention provides a method of preparing said compound or a salt of formula (X), further comprising the step of preparing said compound of formula (XI); comprising:

(j) treating a compound of formula (XII):

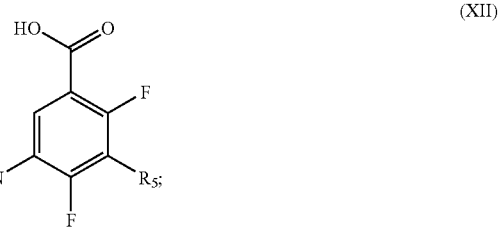

(XII)

wherein $R_5$ is as described above;
with a compound of formula (XIII):

(XIII)

wherein $R_2$ and $R_4$ are as described above; in the presence of a strong base in a solvent.

In another embodiment, the present invention provides a method of preparing said compound or a salt of formula (XI), further comprising the step of preparing said compound of formula (XII); comprising:

(k) treating a compound of formula (XIV):

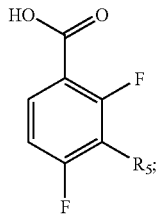

(XIV)

wherein $R_5$ is as described above;
with a nitro-producing agent in a solvent.

In another embodiment, said nitro-producing agent is $HCl/H_2SO_4$.

In another embodiment, the present invention provides a compound of formula (VI):

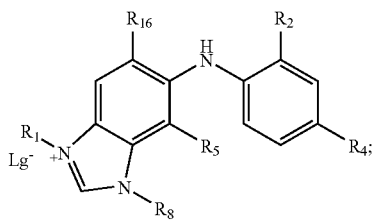

(VI)

wherein $R_1$, $R_2$, $R_4$, $R_5$, $R_8$, $R_{15}$ and Lg are as described above; and $R_{16}$ is —(C=O)—$R_{15}$ or —(C=O)—OH.

In another embodiment, the present invention provides a compound of formula (VIa), which is a compound of formula (VI), wherein $R_{16}$ is —(C=O)—O—$R_3$:

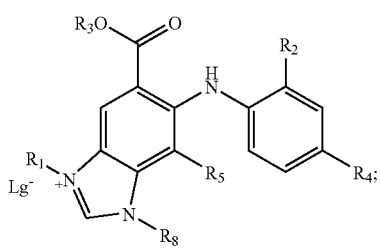

(VIa)

wherein $R_1$, $R_2$, $R_3$, $R_4$, $R_5$, $R_8$, and Lg are as described above.

In another embodiment, the present invention provides a compound of formula (VII):

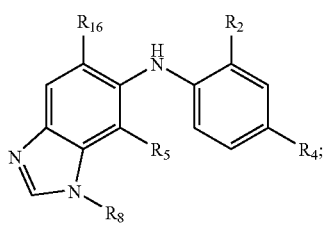

(VII)

wherein $R_2$, $R_4$, $R_5$, $R_8$, and $R_{15}$ are as described above; and $R_{16}$ is —(C=O)—$R_{15}$ or —(C=O)—OH.

In another embodiment, the present invention provides a compound of formula (VIIa), which is a compound of formula (VII), wherein $R_{16}$ is —(C=O)—$OR_3$:

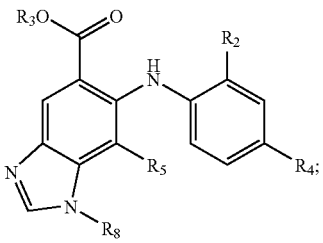

(VIIa)

wherein $R_2$, $R_3$, $R_4$, $R_5$, and $R_8$ are as described above.

The invention also provides a pharmaceutical composition comprising a compound of Formula I and a pharmaceutically acceptable carrier.

Additionally, the invention provides a method of treating a proliferative disease in a patient in need thereof comprising administering a therapeutically effective amount of a compound of Formula I.

Furthermore, the invention provides methods of treating cancer, restenosis, psoriasis, autoimmune disease, atherosclerosis, osteoarthritis, rheumatoid arthritis, heart failure, chronic pain, and neuropathic pain in a patient in need thereof comprising administering a therapeutically effective amount of a compound of Formula I.

In addition, the invention provides a method for treating cancer in a patient in need thereof comprising administering a therapeutically effective amount of a compound of Formula I in combination with radiation therapy or at least one chemotherapeutic agent.

The invention also provides the use of a compound of Formula I for the manufacture of a medicament for the treatment of the disease states or diseases provided above.

DETAILED DESCRIPTION OF THE INVENTION

Certain terms are defined below and by their usage throughout this disclosure.

The terms "halogen" or "halo" in the present invention refer to a fluorine, bromine, chlorine, and iodine atom or fluoro, bromo, chloro, and iodo. The terms fluorine and fluoro, for example, are understood to be equivalent herein.

Alkyl groups, such as "$C_{1-6}$ alkyl", include aliphatic chains (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, isobutyl, sec-butyl, t-butyl, pentyl, 2-pentyl, 3-pentyl, isopentyl, neopentyl, (R)-2-methylbutyl, (S)-2-methylbutyl, 3-methylbutyl, 2,3-dimethylpropyl, hexyl, and the like. The term "$C_{1-6}$ alkyl" includes within its definition the terms "$C_{1-4}$ alkyl" and "$C_{1-2}$ alkyl".

The term "alkoxy" as used herein refers to a straight or branched alkyl chain attached to an oxygen atom. The term "$C_{1-8}$ alkoxy" as used herein refers to a straight or branched alkyl chain having from one to eight carbon atoms attached to an oxygen atom. Typical $C_{1-8}$ alkoxy groups include methoxy, ethoxy, propoxy, isopropoxy, butoxy, t-butoxy, pentoxy and the like. The term "$C_{1-8}$ alkoxy" includes within its definition the terms "$C_{1-6}$ alkoxy" and "$C_{1-4}$ alkoxy".

Alkenyl groups are analogous to alkyl groups, but have at least one double bond (two adjacent sp² carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof. Like alkyl groups, unsaturated groups may be straight chain or branched. Examples of alkenyls and alkynyls include vinyl, allyl, 2-methyl-2-propenyl, cis-2-butenyl, trans-2-butenyl, and acetyl.

Cycloalkyl groups, such as $C_{3-6}$ cycloalkyl, refer to a saturated hydrocarbon ring structure containing from 3 to 6 atoms. Typical $C_{3-6}$ cycloalkyl groups include cyclopropyl, cyclobutyl, cyclopentyl, cyclohexyl, and the like.

The term "aryl" means an unsubstituted aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl).

Heterocyclic radicals, which include but are not limited to heteroaryls, include: furyl, (is)oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their nonaromatic counterparts. Further examples of heterocyclic radicals include thienyl, piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, octahydrobenzofuranyl, (iso)quinolinyl, naphthyridinyl, benzimidazolyl, and benzoxazolyl.

The term "heteroaryl", as used herein, unless otherwise indicated, includes monocyclic aromatic heterocycles containing five or six ring members, of which from 1 to 4 can be heteroatoms selected, independently, from N, S and O, and bicyclic aromatic heterocycles containing from eight to twelve ring members, of which from 1 to 4 can be heteroatoms selected, independently, from N, S and O.

The present invention includes the hydrates and the pharmaceutically acceptable salts and solvates of the compounds defined by Formula I. The compounds of this invention can possess a sufficiently basic functional group, and accordingly react with any of a number of inorganic and organic acids, to form a pharmaceutically acceptable salt.

The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts, include the pharmaceutically acceptable salts listed in *Journal of Pharmaceutical Science,* 1955;66:2–19, which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as ptoluenesulfonic, methanesulfonic acid, benzenesulfonic acid, oxalic acid, pbromophenylsulfonic acid, carbonic acid, succinic acid, citric acid, benzoic acid, acetic acid, and the like. Example of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymateate, mandelate, mesylate, nicotinate, isonicotinate, cinnamate, hippurate, nitrate, stearate, phthalate, teraphthalate, butyne-$_1$,4-dioate, butyne-1,4-dicarboxylate, hexyne-1,4-dicarboxylate, hexyne-1,6-dioate, benzoate, chlorobenzoate, methylbenzoate, hydrozybenzoate, methoxybenzoate, dinitrobenzoate, o-acetoxybenzoate, naphthalene-2-benzoate, phthalate, ptoluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, hemi-tartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartarate, and the like. A preferred pharmaceutically acceptable salt is hydrochloride.

It should be recognized that the particular counterion forming a part of any salt of this inventions is usually not of a critical nature, so long as the salt as a whole is pharmacologically acceptable and as long as the counterion does not contribute undesired qualities to the salt as a whole. It is further understood that such salts may exist as a hydrate.

The enantiomers of compounds of the present invention can be resolved by one of ordinary skill in the art using standard techniques well-known in the art, such as those described by J. Jacques, et al., "Enantiomers, Racemates, and Resolutions", John Wiley and Sons, Inc 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The compounds of Formula I can be prepared by techniques and procedures readily available to one of ordinary skill in the art, for example by following the procedures as set forth in the following Schemes, or analogous variants thereof. These synthetic strategies are further exemplified in examples below. These schemes are not intended to limit the scope of the invention in any way.

As used herein, the following terms have the meanings indicated: "AcOH" refers to acetic acid; "CDI" refers to 1,1'-carbonyldiimidazole; Celite® refers to a filter agent which is acid washed and approximately 95% $SiO_2$; "$CHCl_3$" refers to chloroform; "$CH_2Cl_2$" and "DCM" refer to dichloromethane; "conc." refers to concentrated; "DABCO" refers to 1,4-diazabicyclo[2.2.2]octane; "DIEA" refers to N,N-diisopropylethylamine; "DMA" refers to N,N-dimethylacetamide; "DMF" refers to N,N-dimethylformamide; "DMSO" refers to methyl sulfoxide; "DMT-MM" refers to 4-(4,6-dimethoxy-1,3,5-triazin-2-yl)-4-methylmorpholinium chloride; "EtOAc" refers to ethyl acetate; 'EtOH" refers to ethanol; "$Et_2O$" refers to diethyl ether; "FMOC" refers to 9H-fluoren-9-ylmethyl ester; "h" refers to hours; "HCl" refers to hydrochloric acid; "Me" refers to methyl;

"MeOH" refers to methanol; "Me$_2$SO$_4$" refers to dimethyl sulfate; "min" refers to minutes; "NaOH" refers to sodium hydroxide' "Na$_2$SO$_4$ refers to sodium sulfate; "N-MM" refers to N-methylmorpholine; "Pd/C" refers to palladium on carbon; "PE" refers to petroleum ether which can be substituted with hexanes; "(Ph$_3$P)$_2$PdCl$_2$" refers to dichlorobis(triphenylphosphine)palladium(II); "(Ph$_3$P)$_4$Pd" refers to tetrakis (triphenylphosphine) palladium (0); "PS" refers to polymer—supported; "R.T." refers to room temperature; "sat" refers to saturated; "TEA" refers to triethylamine; "TFA" refers to trifluoroacetic acid; "THF" refers to "tetrahydrofuran; "TLC" refers to thin layer chromatography and "TMS" refers to trimethylsilyl. All other terms and substituents, unless otherwise indicated, are previously defined.

All other terms and substituents, unless otherwise indicated, are previously defined. The reagents and starting materials are readily available to one of ordinary skill in the art.

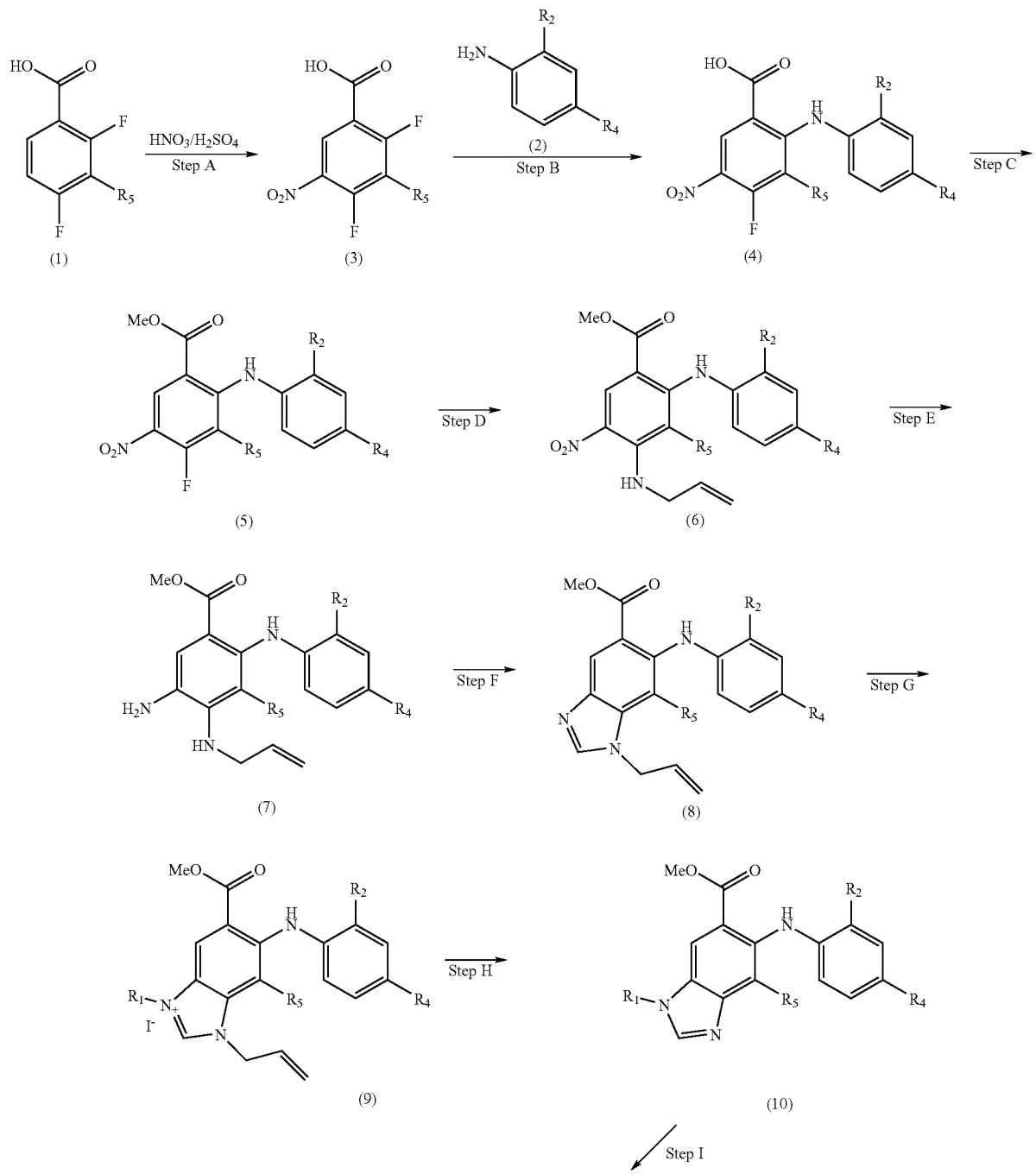

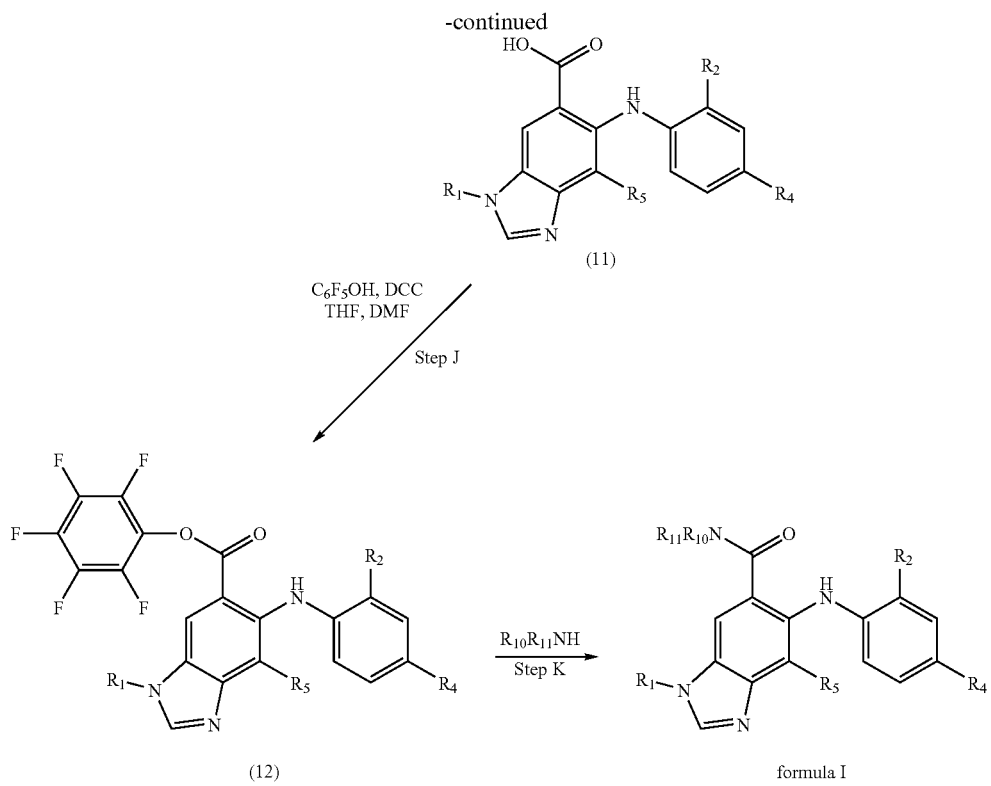

Scheme 1 provides syntheses of the compounds of Formula I.

$R_{10}$ and $R_{11}$ are independently hydrogen, amino, alkyl, substituted alkyl, alkoxy or substituted alkoxy.

In Scheme 1, Step A, a suitable benzoic acid derivative (1) is converted to the nitrobenzoic acid derivative (3) by a procedure known to one of skill in the art.

In Scheme 1, Step B, the 2-(arylamino)-5-nitrobenzoic acid derivative (4) is prepared from the coupling of the nitrobenzoic acid derivative (3) and a suitable aniline (2) in the presence of a strong base, for example, lithium bis(trimethylsilyl)amide (LiHMDS) or lithium diisopropylamide, in a polar aprotic solvent such as tetrahydrofuran, acetonitrile or dimethylformamide. For example, the aniline (2) and the nitrobenzoic acid (3) are dissolved in a suitable organic solvent and cooled to about −58° C. under nitrogen. The suspension is treated with an excess of a suitable base, such as the lithium base, LiHMDS, and allowed to warm to room temperature. The reaction is typically complete within about 2 hours to about 5 days. The resulting nitrobenzoic acid derivative (4) can be isolated by removing the solvent, for example by evaporation under reduced pressure or by filtering the precipitated solid through Celite® and washing with a suitable solvent. The nitrobenzoic acid derivative (4) can be further purified, if desired, by standard methods such as chromatography, crystallization, or distillation.

In Scheme 1, Step C, the nitrobenzoic acid derivative (4) is converted to the methyl ester derivative (5) by a procedure generally known in the art. For example, the nitrobenzoic acid derivative (4) in a suitable solvent is treated with sodium bicarbonate followed by a dimethylsulfate.

In Scheme 1, Step D, a suitable amine, such as allylamine was added to the methyl ester derivative (5) in a suitable solvent system such as, methanol, THF and water, to provide the alkynyl-amino methyl ester derivative (6).

In Scheme 1, Step E, the nitro substituent of the alkenyl-amino methyl ester derivative (6) was converted to the corresponding amine (5) according to a procedure known in the art. For example, the nitro methyl ester derivative (6) is treated with ammonium chloride in a mixture of a suitable solvent, such as methanol, and dioxane. Iron powder is added under nitrogen and the entire mixture is refluxed to provide the amine (5).

In Scheme 1, Step F, the benzamidazole (8) is formed from the amine (5). For example, the amine (5) in a suitable solvent, such as methanol, is treated with formamidine acetate and refluxed under nitrogen to provide the benzamidazole (8).

In Scheme 1, Step G, benzamidazole (8) is converted to a substituted benzamidazole (9) by treating the benzamidazole (8) with iodomethane in a suitable solvent, such as acetonitrile.

In Scheme 1, Step H, substituted benzamidazole (9) is deprotected to provide the compound (10).

In Scheme 1, Step I, compound (10) is treated with potassium trimethyl silanolate in a solvent, such as THF/water.

In Scheme 1, Step J, a compound (11) is reacted with an active ester, in the presence of a base, if necessary, to produce an activated compound (12). Preferred active esters include pentafluorophenyl tnfluoroacetate and preferred bases include diisopropylethylamine, triethylamine, 4-methylmorpholine, pyridine or a substituted pyridine, for example, 4-dimethylaminopyridine or 2,6-dimethylpyridine. Preferred solvents are polar aprotic solvents such as dichloromethane, tetrahydrofuran, dimethylformamide, or N,N-dimethylacetamide.

In Scheme 1, Step K, the compounds of formula I are generally obtained by the union of a compound (12) with amine or alkoxylamine in the presence of a base, if necessary. Preferred bases include diisopropylethylamine, triethylamine, 4-methylmorpholine, pyridine or a substituted pyridine, for example, 4-dimethylaminopyridine or 2,6-dimethylpyridine. Preferred solvents are polar aprotic solvents such as dichloromethane, tetrahydrofuran, dimethylformamide, or N,N-dimethylacetamide. The reactions are generally carried out at a temperature between about −58° C. to about 25° C., and are normally complete within about 1 hour to about 5 days. The product amide can be isolated by removing the solvent, for example by evaporation under reduced pressure, and further purified, if desired, by standard methods such as chromatography, crystallization, or distillation.

Scheme 2

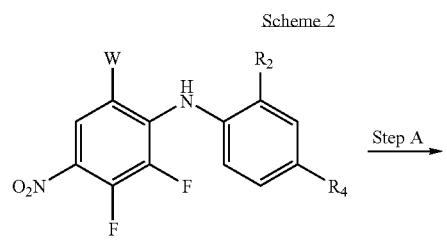

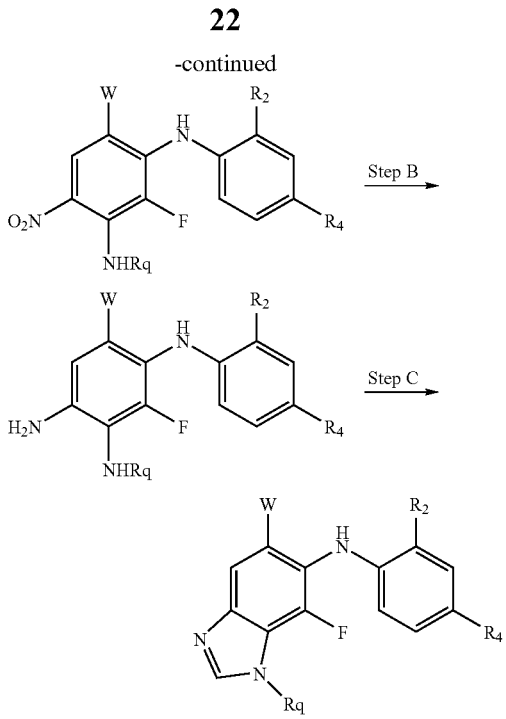

In Scheme 2, protecting groups Rq other than allyl may also be used. Steps A, B, and C of Scheme 2 can be performed analogous to Scheme 1.

Scheme 3

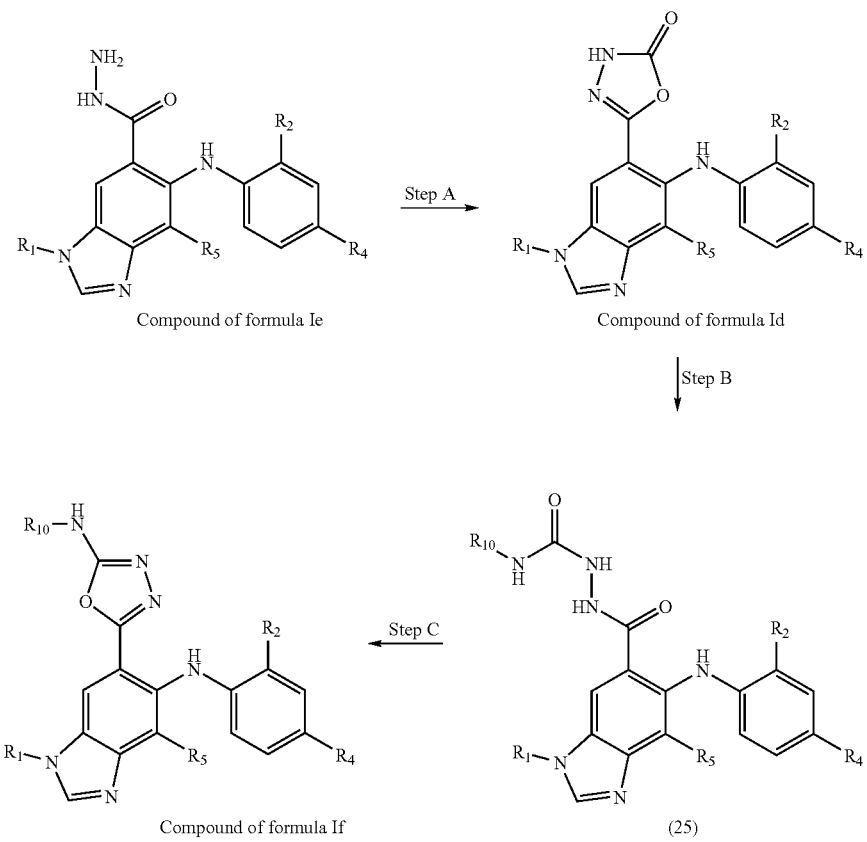

In Scheme 3, Step A, an acyl hydrazide of formula Ie is converted to an oxadiazolinone of formula Id. A preferred reagent is carbonyldiimidazole in polar aprotic solvents such as dimethylformamide.

In Scheme 3, Step B, compound (25) is obtained by the union of oxadiazolinone (Id) with an alkyl amine or substituted alkylamine. Preferred solvents for this transformation include pyridine, isopropanol and ethanol at temperatures between 80° C. and 120° C. Reactions are generally complete between 1 h and 5 days.

In step C, the urea (25) is subjected to conditions of cyclodehydration to afford oxadiazoles for formula If. Preferred conditions for this transformation are the combination of carbon tetrachloride and triphenyphosphine (or polymer-supported triphenylphoshine) and a base such as triethylamine. Preferred solvents for this transformation include dichloromethane or 1,2-dichloroethane at temperatures between 35° C. and 100° C. During the cyclodehydration step, hydroxyl or amino substituents on the $R_{10}$ alkyl chain may be chemically protected, if necessary, using protecting groups familiar to those skilled in the art. Accordingly, a protection/deprotection sequence, if necessary, is implicit in Step C. For hydroxyl substituents on $R_{10}$, preferred protecting groups include silyl ethers, for example tert-butyldimethylsilyl ethers, triethylsilyl ethers, or triisopropylsilyl ethers. Such silyl ethers are chemically removed using fluoride. Preferred reagents for this deprotection include tetrabutylamonium floride or cesium fluoride.

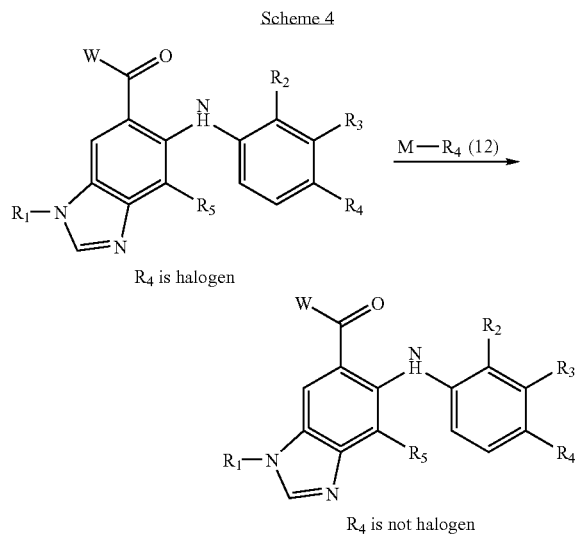

In Scheme 4, the compounds of formula I, wherein $R_4$ is not halogen are prepared from the compounds of formula I wherein $R_4$ is halogen, by transition metal-promoted coupling with reagent M-$R_4$ wherein $R_4$ is non-halogen (12) in a suitable solvent or solvents such as triethylamine, tetrahydrofuran or dimethylformamide. The transition metal-promoted coupling may be carried out with a palladium(0) or palladium (II) coupling agent, such as $(Ph_3P)_4Pd$ or $(Ph_3P)_2PdCl_2$. The entire mixture is stirred from about 2 to 24 hours at room temperature. M is defined as a functional group known to transfer a carbon radical fragment in transition metal-promoted coupling processes. Examples of a suitable M group include trialkylstannyl, trialkylsilyl, trimethylsilyl, zinc, tin, copper, boron, magnesium and lithium. Examples of a suitable M-$R_4$ reagent (12) when, $R_4$ is $C_{2-4}$ alkenyl is allyltributyltin or tetravinyltin, and when $R_4$ is —OH-substituted $C_{2-6}$ alkynyl is propargyl alcohol. Preferred halogens, when $R_4$ is halogen, are bromine and iodine.

The resulting compound of formula I, as well as the protected Formula I compound, can be isolated by removing the solvent, for example by evaporation under reduced pressure, and further purified, if desired, by standard methods such as chromatography, crystallization, or distillation.

It would be understood by one of skill in the art that the substituent $R_4$, when $R_4$ is non-halogen, may be further transformed, such as by oxidation, reduction, deprotection, or hydrogenation.

A compound wherein $R_4$ is $C_{2-4}$ alkenyl may be transformed to a compound wherein $R_4$ is —OH-substituted alkyl by treating the double bond of the alkene with ozone and $NaBH_4$. Furthermore, a compound wherein $R_4$ is $C_{2-4}$ alkenyl may be transformed to a compound wherein $R_4$ is alkyl substituted with $_2$ —OH substituents by treating the double bond of the alkene with $OsO_4$.

A compound wherein $R_4$ is an alkene or alkyne derivative may be reduced under conditions known in the art, such as through hydrogenation, such as with Pd/C under an atmosphere of hydrogen. For example, the alkyne derivative is dissolved in a suitable solvent, such as absolute ethanol, in the presence of a metal catalyst, such as palladium on carbon. This mixture is stirred under an atmosphere of hydrogen from about 1 to 24 hours at room temperature to provide the fully saturated derivative. Alternately, the alkyne derivative is partially reduced via hydrogenation to provide the alkene derivative. For example, the alkyne derivative is dissolved in a suitable solvent, such as tetrahydrofuran, in the presence of a catalyst, such as Lindlar catalyst or palladium on carbon and, if desired, a suitable compound which disrupts the actions of the catalyst, such as quinoline or pyridine. This mixture is stirred under an atmosphere of hydrogen from about 1 to 24 hours at room temperature to provide the alkene derivative.

The substituent $R_4$ may also be transformed into a different $R_4$ through standard synthetic procedures known to one of skill in the art.

It would be understood by one of skill in the art that the transformation of $R_4$ as shown in Scheme 4 may be performed at various steps throughout the synthesis of compounds of the present invention, as desired. For example, $R_4$ may be transformed before the coupling of the ester (1) and aniline (2) as shown in Scheme 1, Step A.

Further transformations of $R_4$ are shown in Scheme 5

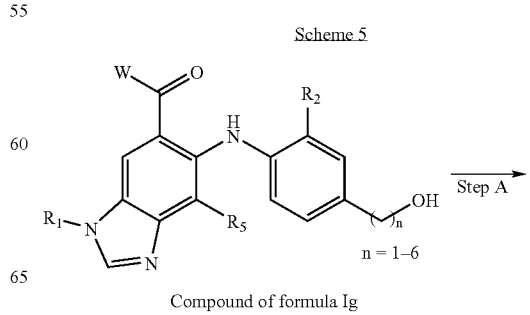

Compound of formula Ig

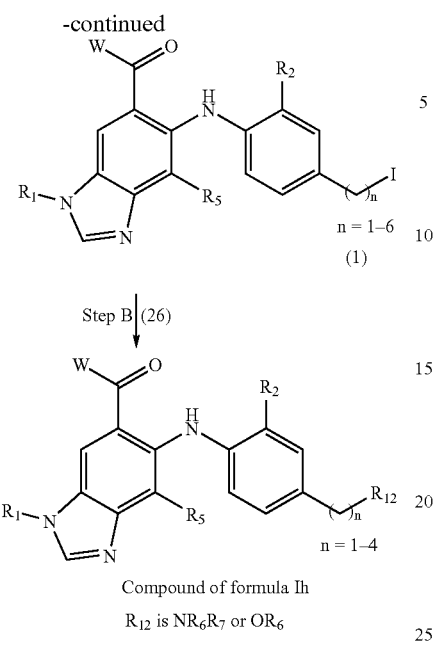

Compound of formula Ih

R$_{12}$ is NR$_6$R$_7$ or OR$_6$ below.

In Scheme 5, step A, the compound of formula Ig is dissolved in a suitable solvent such as tetrahydrofuran and reacted with methanesulfonyl chloride to give the intermediate mesylate, then NaI in EtOAc to give the iodide compound (26).

In Scheme 5, step B, the iodide compound (26) is reacted with a suitable amine, such as methylamine or dimethylamine, or a suitable alkoxide to give compounds of formula Ih.

It would also be understood by one of skill in the art that an aniline (2), see Scheme 1 above, may be prepared to include the desired R$_4$.

The suitable aniline (2), see Scheme 1 above, can be prepared by techniques and procedures readily available to one of ordinary skill in the art and by following the procedures as set forth in the following Schemes, or analogous variants thereof. Additionally, anilines (2) are taught in U.S. Ser. No. 10/349,801 filed Jan. 23, 2003 and U.S. Ser. No. 10/349,826 filed Jan. 23, 2003, the disclosure of which is hereby incorporated by reference. These Schemes are not intended to limit the scope of the invention in any way.

Scheme 6

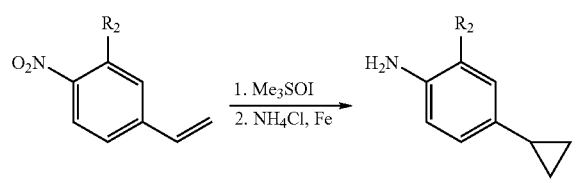

*Bull. Soc. Chim. Belg.*, 95(2), 135–8; 1986

In Scheme 6, a suitably substituted para-nitrostyrene is reacted with dimethyloxosulfonium methylide to form the substituted para-nitrocyclopropylbenzene. Reduction of para-nitrocyclopropylbenzene with iron in the presence of weak acid gives the desired aniline.

Scheme 7

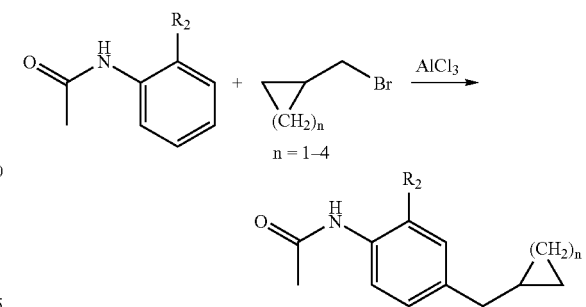

In Scheme 7, the suitable ortho-substituted acetamide is reacted with bromocyclobutane, bromocyclopropane, or bromocyclohexane under typical Friedel-Craft conditions, as known to one of skill in the art, to give the desired para-cycloalkylanilines. The acetamide is deprotected under conditions known to one of skill in the art to provide the desired para-cycloalkylmethylanilines.

Scheme 8

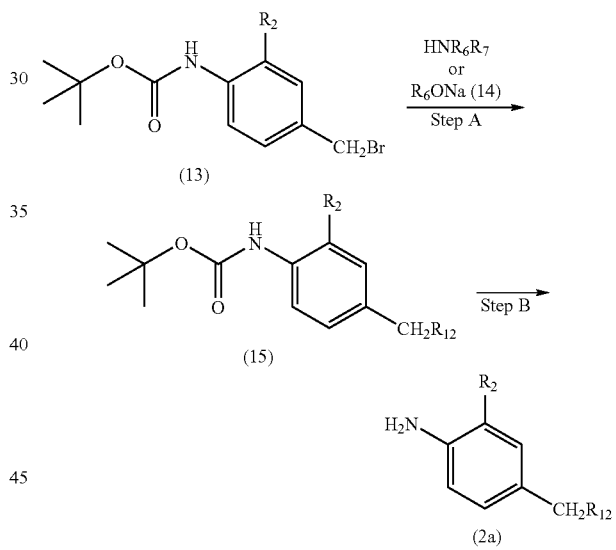

In Scheme 8, Step A, a suitable amine or alkoxide (14) is reacted with a 4-tert-butoxycarbonylamino-3-substituted-benzyl bromide (13), such as 4-tert-butoxycarbonylamino-3-fluorobenzyl bromide (*J. Med. Chem.*, 2000;43:5015). In Step B, the BOC protecting group of compound of structure (15) is hydrolized with, for example, TFA, to provide the desired aniline (2a).

Scheme 9

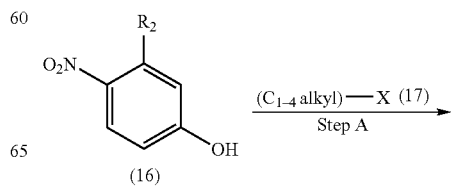

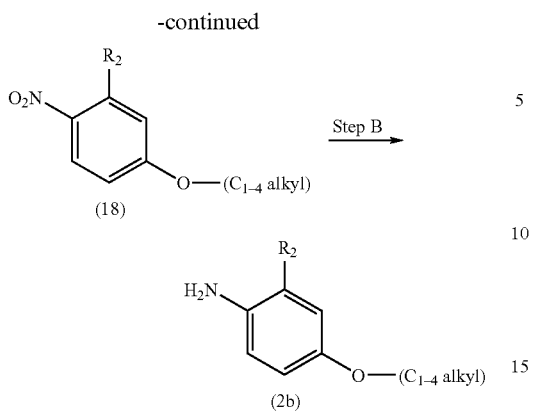

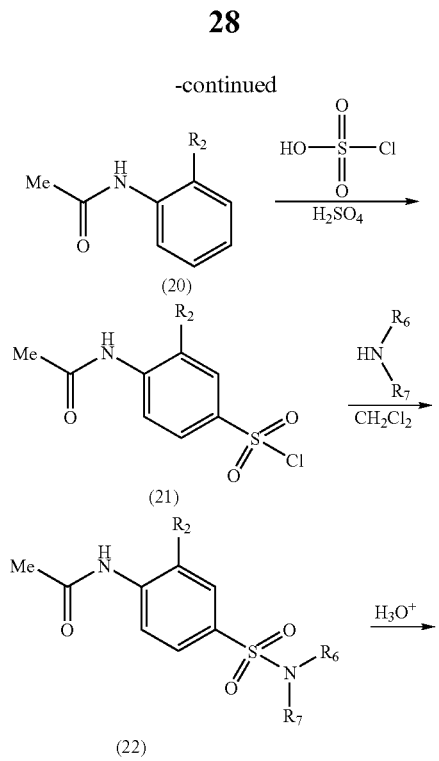

In Scheme 9, Step A, a suitable 3-substituted-4-nitrophenol (16), such as 3-fluoro-4-nitrophenol, is alkylated with a compound of structure (17) in the presence of a suitable base to provide a compound of structure (18). In Step B, compound (18) is reduced via hydrogenation in the presence of a metal catalyst, such as palladium on carbon, in an atmosphere of hydrogen to provide the desired aniline (2b).

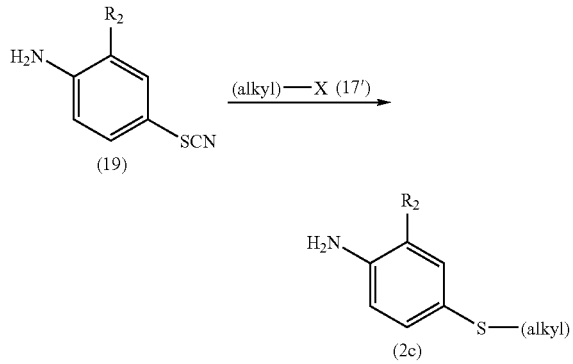

In Scheme 10, a suitable 4-(aminophenyl)thiocyanate (19), is alkylated with a compound of structure (17') in the presence of a suitable nucleophilic base to provide an alkylthio compound of structure (2c). After reaction under standard conditions to form the diphenylamine (3), wherein $R_4$ is —S—(alkyl), as in Scheme 1 above, this compound is then oxidized to the corresponding sulfonyl compound, also generally, the diphenylamine (3), wherein $R_4$ is —SO$_2$—(alkyl).

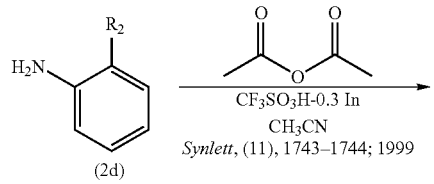

In Scheme 11, the proper ortho-substituted or unsubstituted aniline (2d) is acetylated 10 with acetic anhydride in the presence of trifluoromethanesulfonic acid indium salt to give the protected aniline (20). Chlorosulfonation in the typical manner, as known in the art, gives the sulfonyl chloride derivative (21) which is reacted with an excess of a suitable amine in a solvent such as dichloromethane or dichloroethane to give the protected para-aminobenzenesulfonamide (22). Acid-mediated deprotection in the appropriate solvent gives the desired aniline (2e).

Alternatively, the desired aniline (2e) wherein $R_2$ is methyl, fluorine or chlorine, using compound (21) as the starting material can be prepared. Where $R_2$ is fluorine, the sulfonyl chloride derivative (21) is a compound known in the literature (German Patent DE 2630060, 1958). Similarly, where $R_2$ is methyl, the sulfonyl chloride derivative (21) is also known in the literature (German Patent. DE 2550150, 1958). Finally, the sulfonyl chloride derivative (21) where $R_2$ is chlorine is commercially available.

In addition to the procedure described in Scheme 11, one of ordinary skill in the art would appreciate that there are numerous ways of acetylating anilines. For example, heating the aniline and acetic anhydride together in a suitable solvent, such as acetic acid, would achieve the same result.

Compounds of the present invention also include, but are not limited to the following compounds:

| Compound Number | Structure |
|---|---|
| 1 | 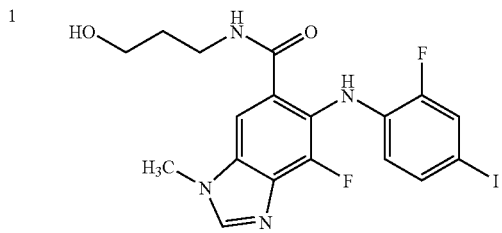 |
| 2 | 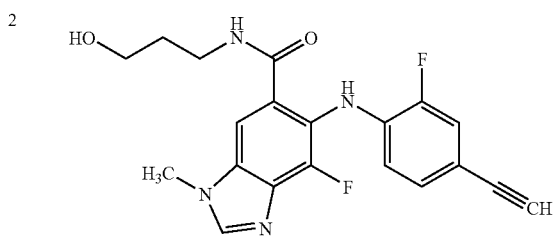 |
| 3 | 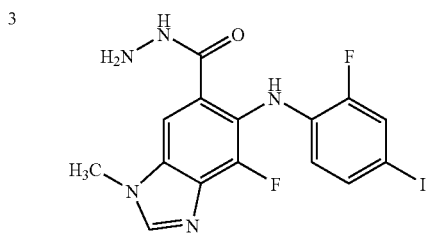 |
| 4 | 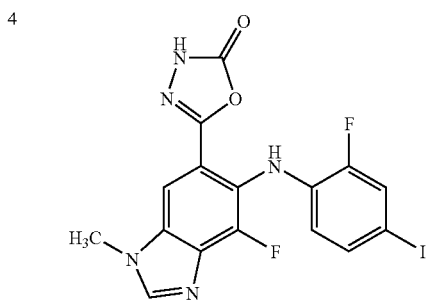 |
| 5 | 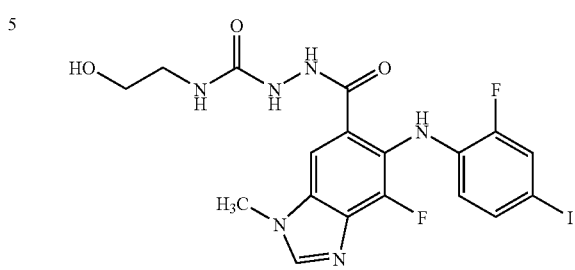 |

-continued
| Compound Number | Structure |
|---|---|
| 6 | 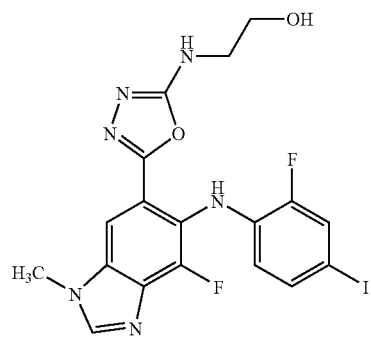 |
| 7 | 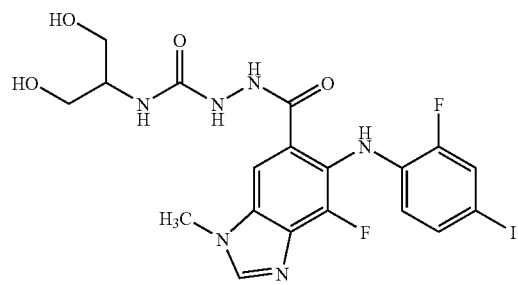 |
| 8 | 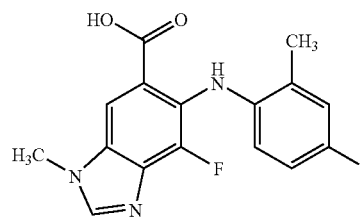 |
| 9 | 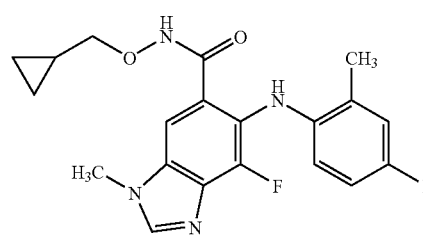 |
| 10 | 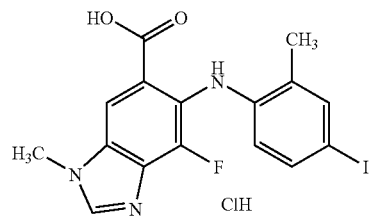 |
| 11 | 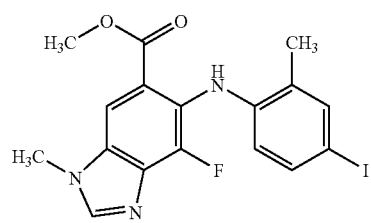 |

-continued
| Compound Number | Structure |
|---|---|
| 12 | 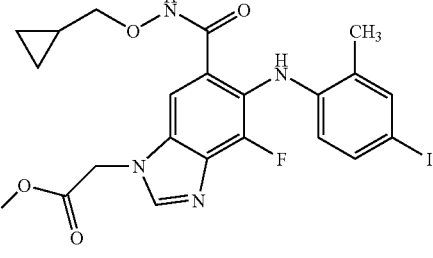 |
| 13 | 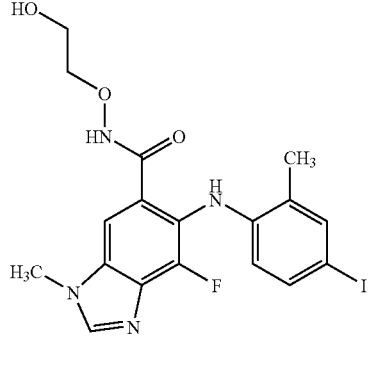 |
| 14 | 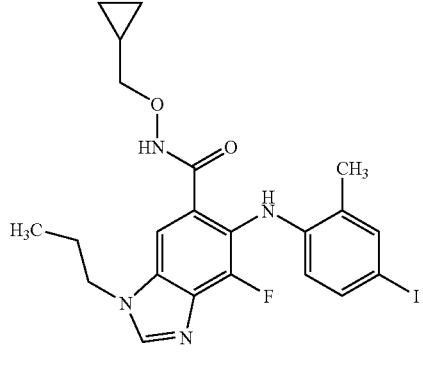 |
| 15 | 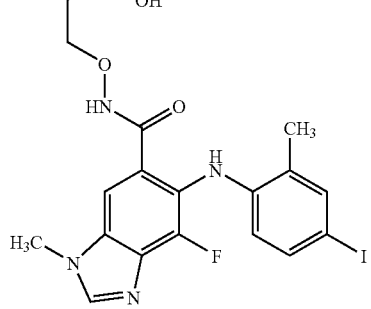 |

-continued
| Compound Number | Structure |
|---|---|
| 16 | 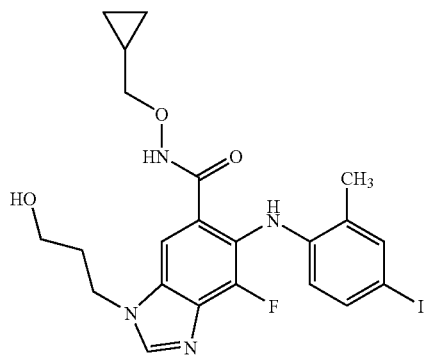 |
| 17 | 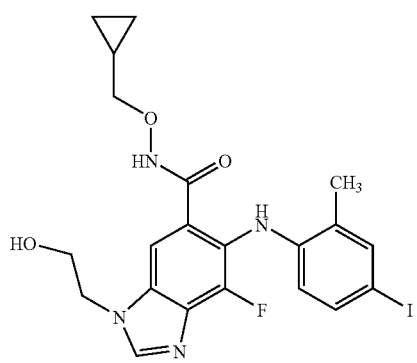 |
| 18 | 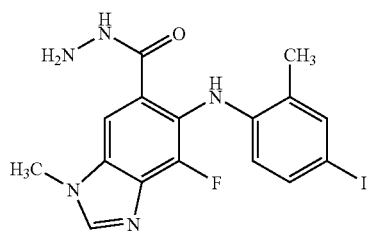 |
| 19 | 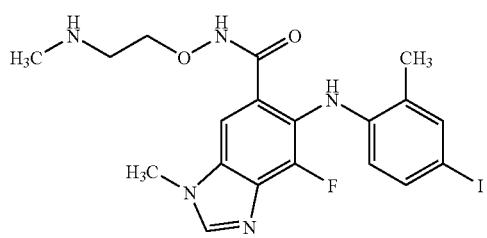 |
| 20 | 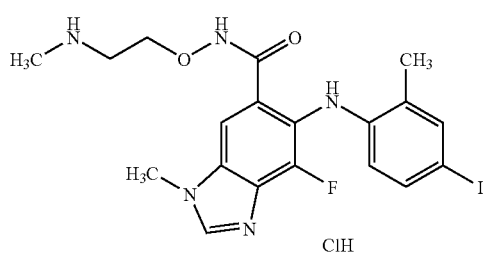 |

-continued

| Compound Number | Structure |
|---|---|
| 21 | 5-(2-amino-1,3,4-oxadiazol-5-yl)-4-fluoro-6-[(4-iodo-2-methylphenyl)amino]-1-methyl-1H-benzimidazole |
| 22 | 4-fluoro-6-[(4-iodo-2-methylphenyl)amino]-1-methyl-1H-benzimidazole-5-carboxamide |
| 23 | 4-fluoro-6-[(2-fluoro-4-iodophenyl)amino]-1-methyl-1H-benzimidazole-5-carboxamide |
| 24 | N-(2,3-dihydroxypropyl)-4-fluoro-6-[(2-fluoro-4-iodophenyl)amino]-1-methyl-1H-benzimidazole-5-carboxamide |
| 25 | 4-fluoro-6-[(2-fluoro-4-iodophenyl)amino]-N-(2-hydroxyethyl)-1-methyl-1H-benzimidazole-5-carboxamide |
| 26 | 4-fluoro-6-[(2-fluoro-4-iodophenyl)amino]-N-(3-hydroxypropyl)-1-methyl-1H-benzimidazole-5-carboxamide |

-continued
| Compound Number | Structure |
|---|---|
| 27 | 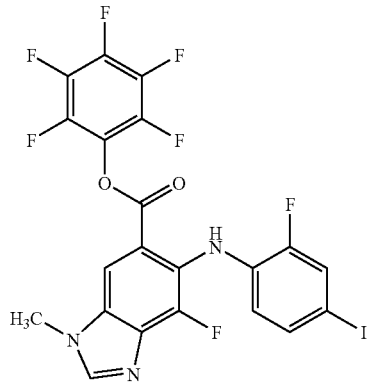 |
| 28 | 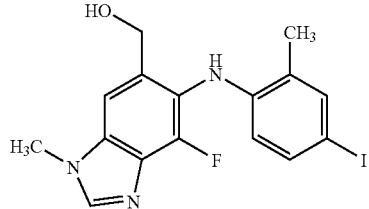 |
| 29 | 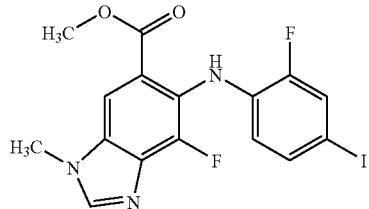 |
| 30 | 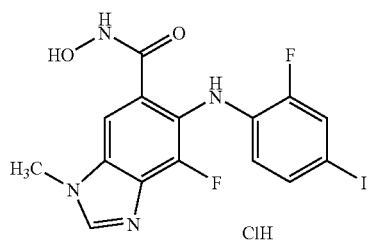 ClH 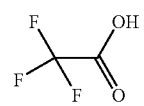 |
| 31 | 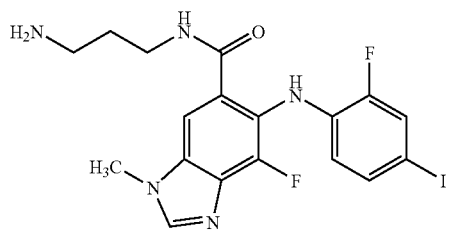 |

-continued
| Compound Number | Structure |
|---|---|
| 32 | 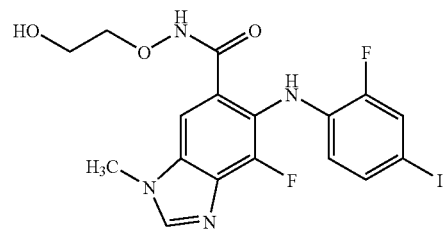 |
| 33 | 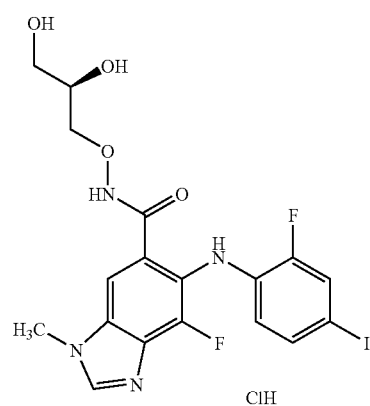ClH |
| 34 | 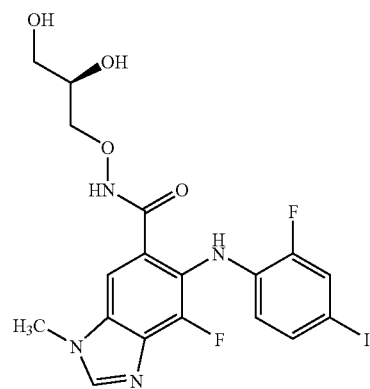 |
| 35 | 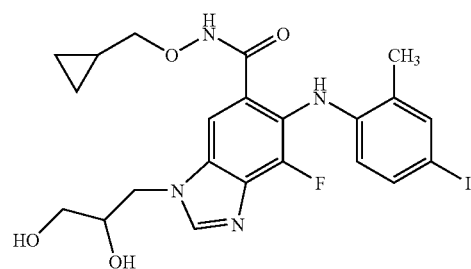 |

-continued
| Compound Number | Structure |
|---|---|
| 36 | 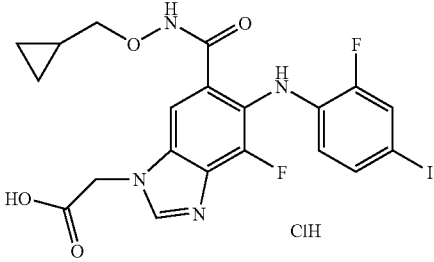 ClH |
| 37 | 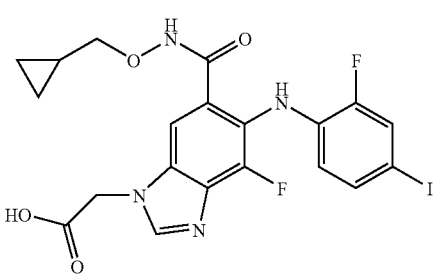 |
| 38 | 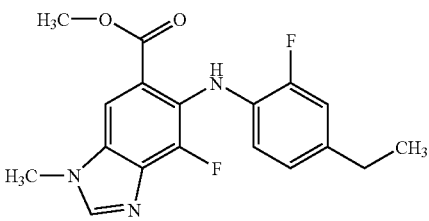 |
| 39 | 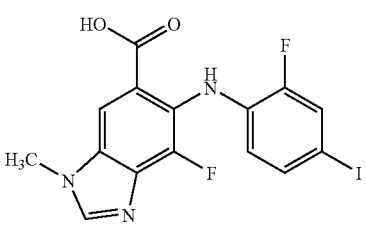 |
| 40 | 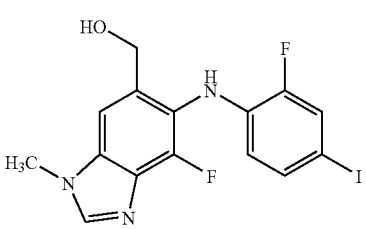 |
| 41 | 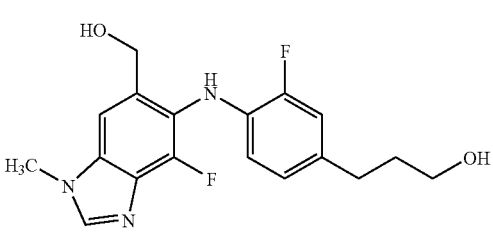 |

-continued
| Compound Number | Structure |
|---|---|
| 42 | 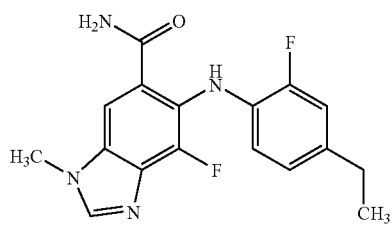 |
| 43 | 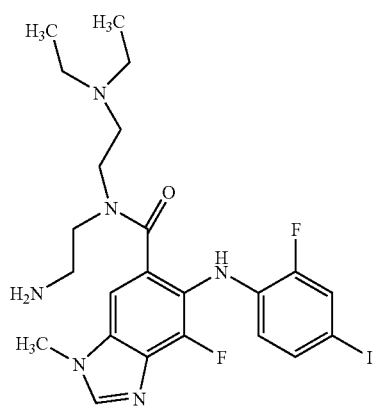 |
| 44 | 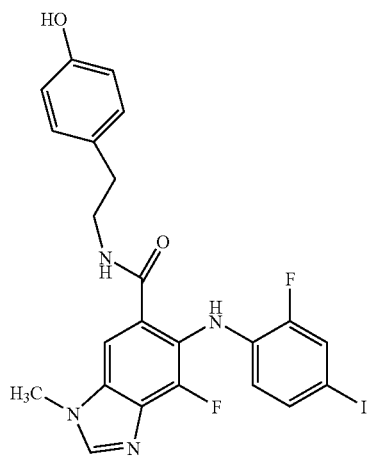 |
| 45 | 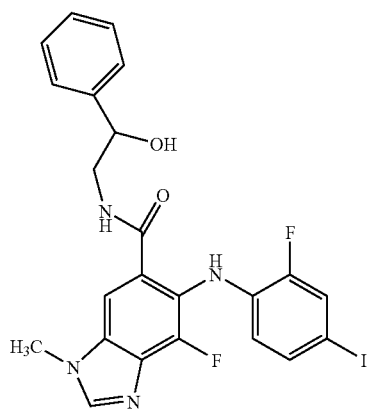 |

-continued
| Compound Number | Structure |
|---|---|
| 46 | 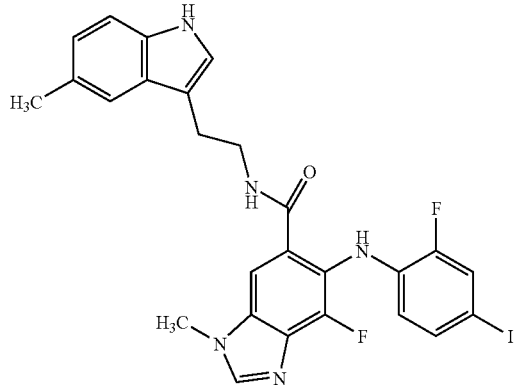 |
| 47 | 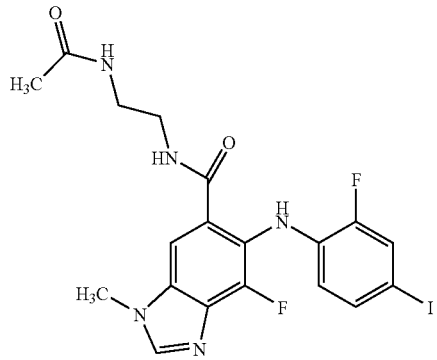 |
| 48 | 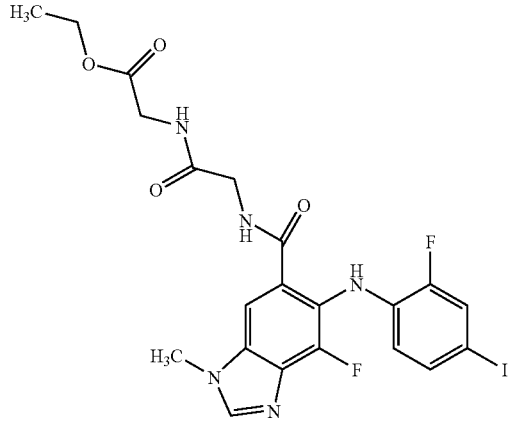 |

-continued
| Compound Number | Structure |
|---|---|
| 49 | 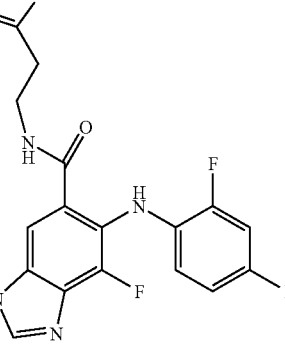 |
| 50 | 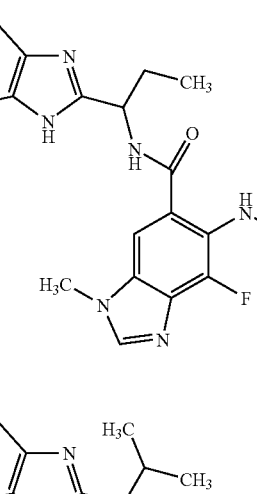 |
| 51 | 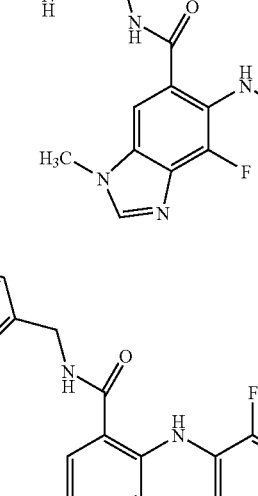 |
| 52 | 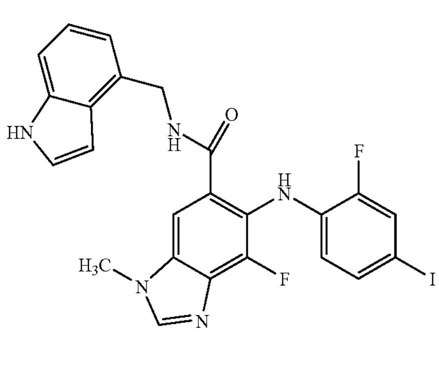 |

-continued
| Compound Number | Structure |
|---|---|
| 53 | 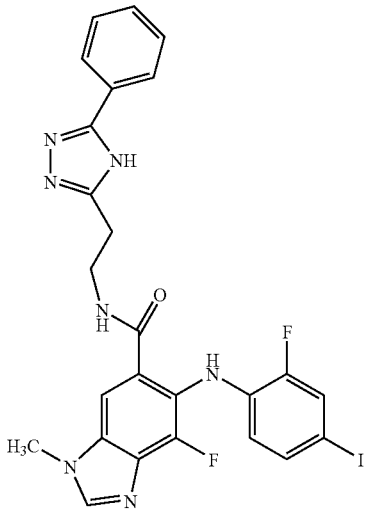 |
| 54 | 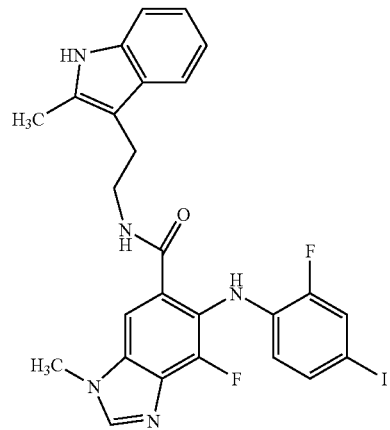 |
| 55 | 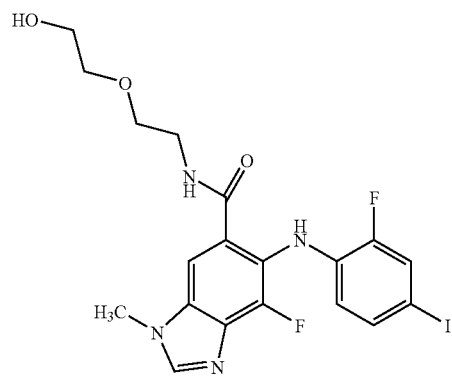 |

-continued
| Compound Number | Structure |
|---|---|
| 56 | 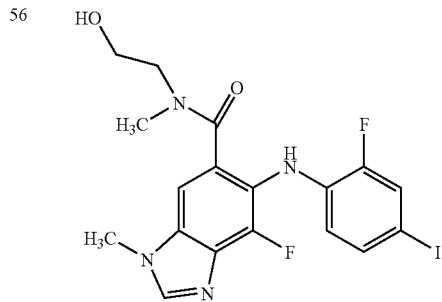 |
| 57 | 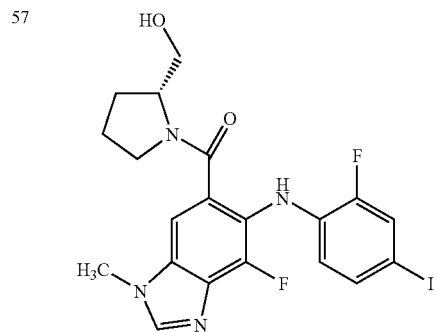 |
| 58 | 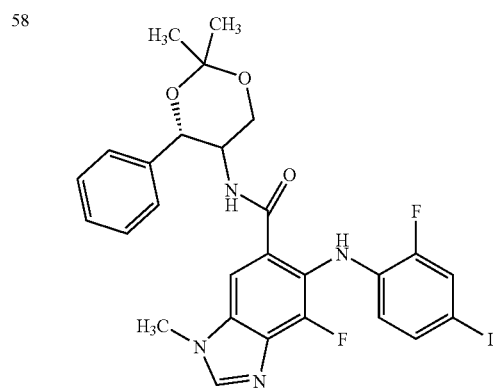 |
| 59 | 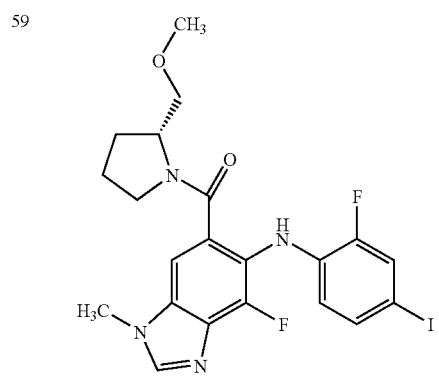 |

-continued
| Compound Number | Structure |
|---|---|
| 60 | 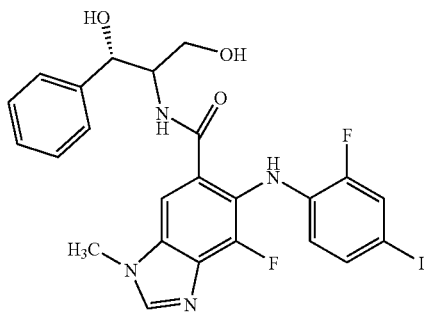 |
| 61 | 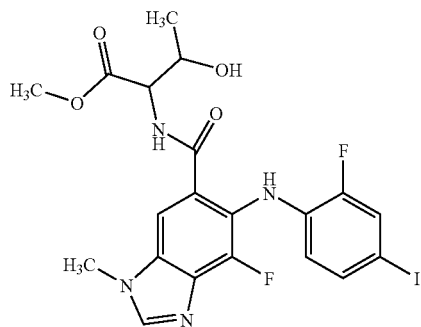 |
| 62 | 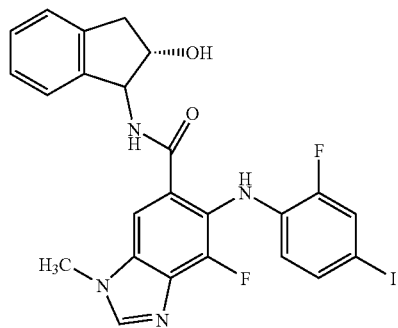 |
| 63 | 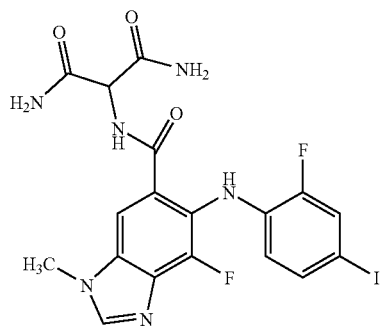 |

| Compound Number | Structure |
|---|---|
| 64 | (structure) |
| 65 | (structure) |
| 66 | (structure) |
| 67 | (structure) |

-continued
| Compound Number | Structure |
|---|---|
| 68 | 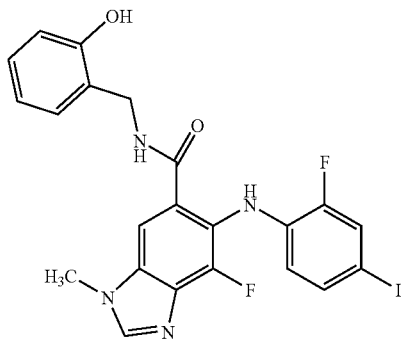 |
| 69 | 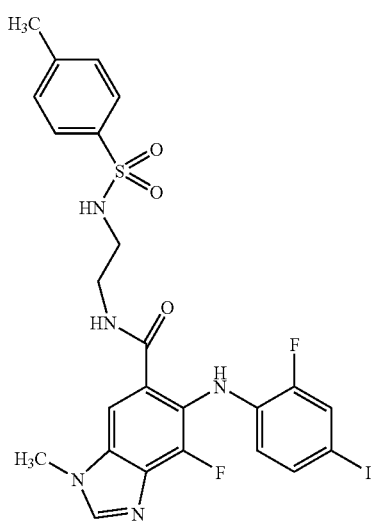 |
| 70 | 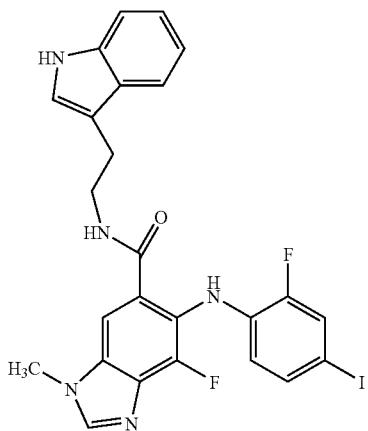 |

-continued
| Compound Number | Structure |
|---|---|
| 71 | 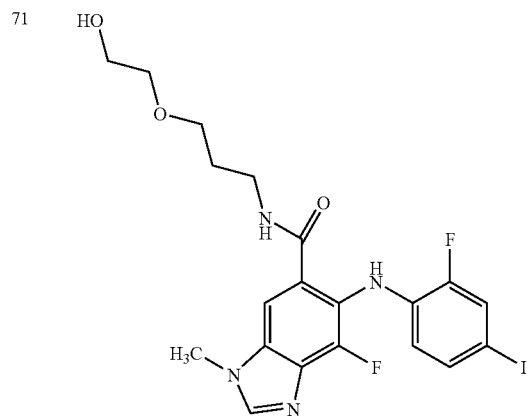 |
| 72 | 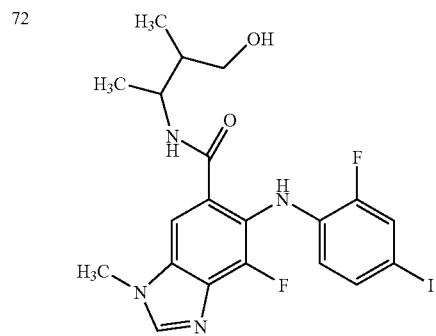 |
| 73 | 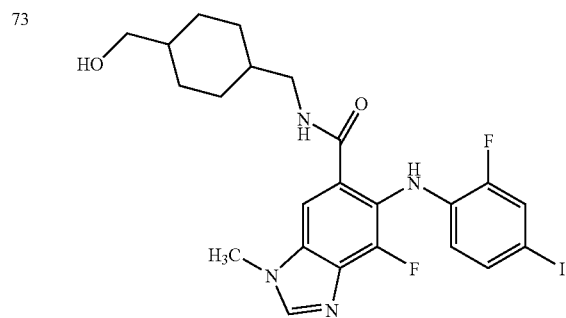 |
| 74 | 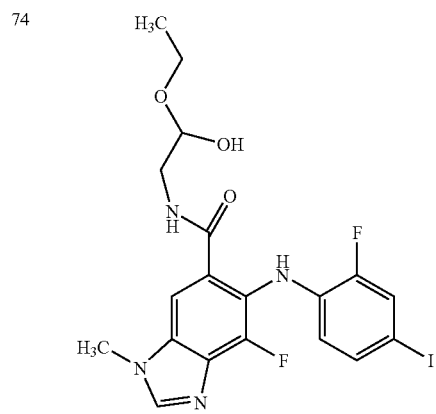 |

-continued
| Compound Number | Structure |
|---|---|
| 75 | 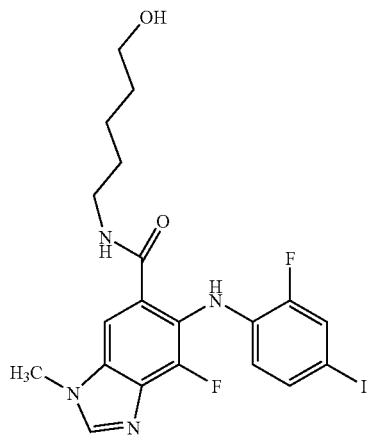 |
| 76 | 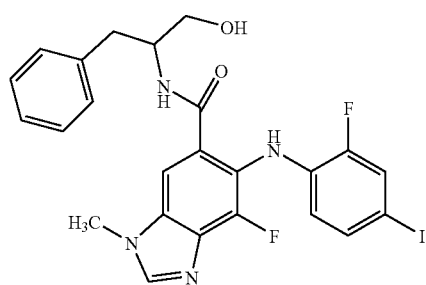 |
| 77 | 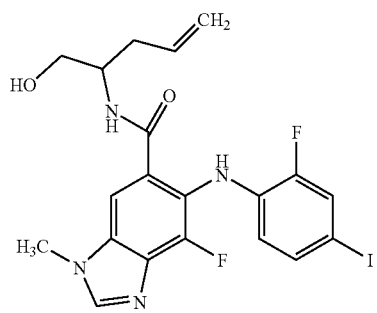 |
| 78 | 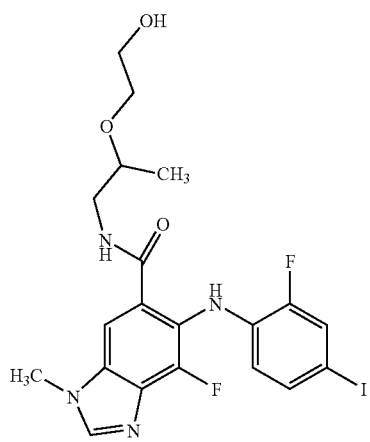 |

-continued
| Compound Number | Structure |
|---|---|
| 79 | 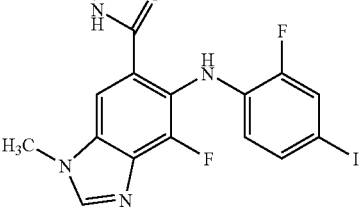 |
| 80 | 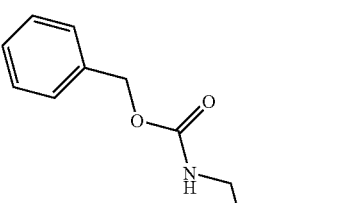 |
| 81 | 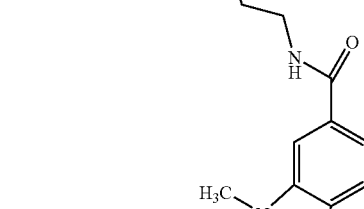 |
| 82 | 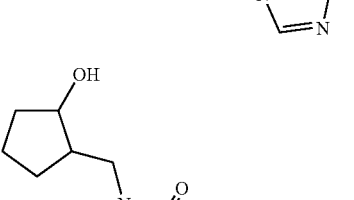 |

-continued
| Compound Number | Structure |
|---|---|
| 83 | 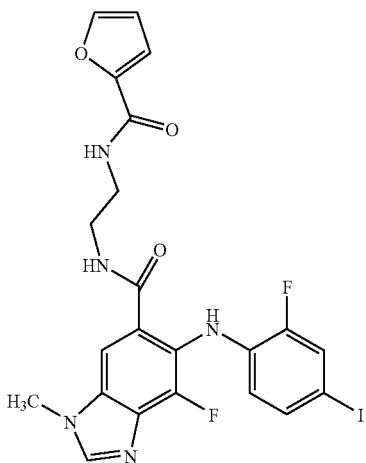 |
| 84 | 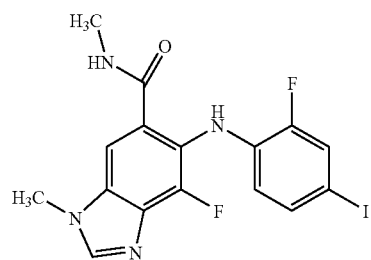 |
| 85 | 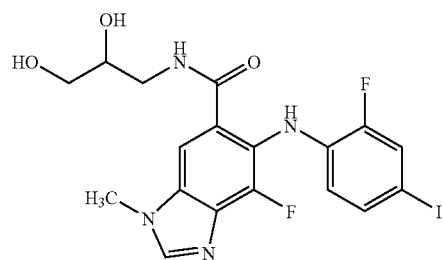 |
| 86 | 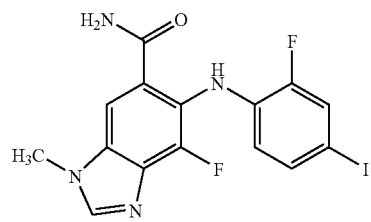 |
| 87 | 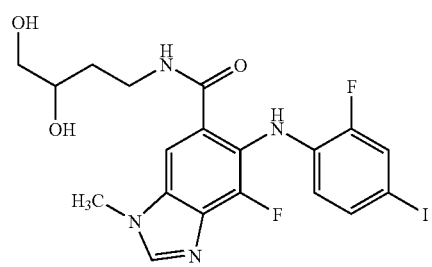 |

Compounds of the present invention also include, but are not limited to the following compounds:
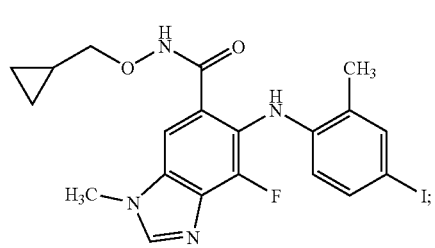
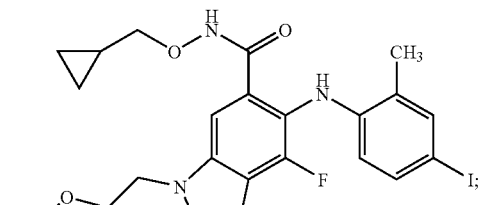
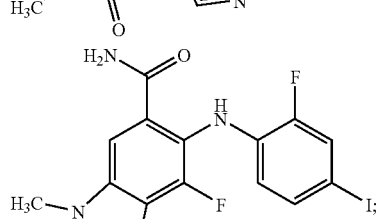
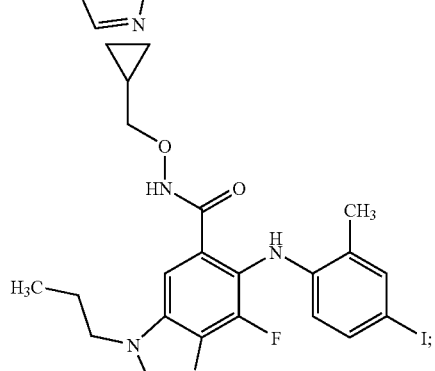
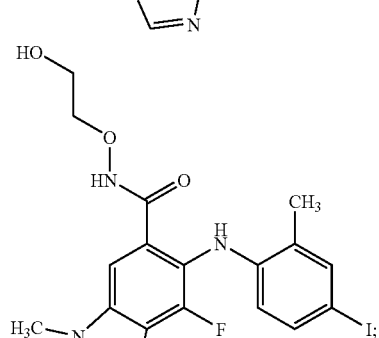
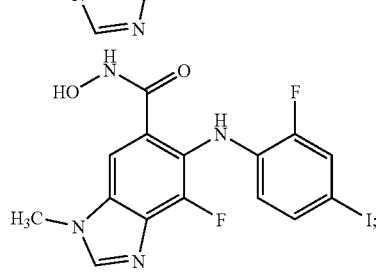
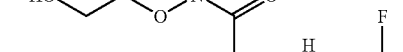
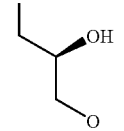
and the pharmaceutically acceptable salts thereof.
In an embodiment, compounds of the present invention also include
and a pharmaceutically acceptable salt thereof.

In another embodiment, compounds of the present invention also include

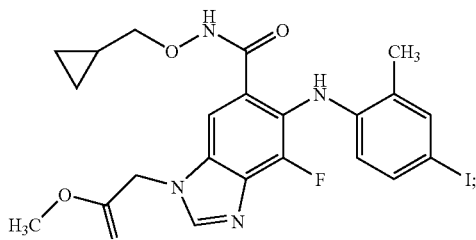

and a pharmaceutically acceptable salt thereof.

In another embodiment, compounds of the present invention also include

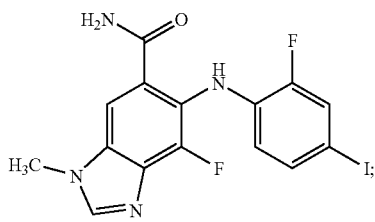

and a pharmaceutically acceptable salt thereof.

In another embodiment, compounds of the present invention also include

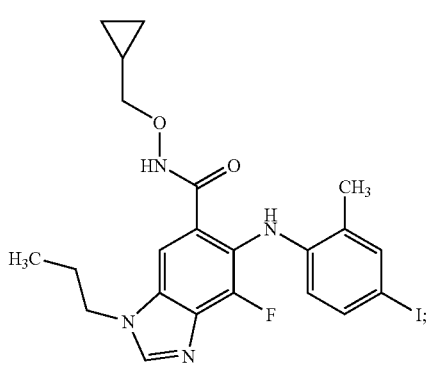

and a pharmaceutically acceptable salt thereof.

In another embodiment, compounds of the present invention also include

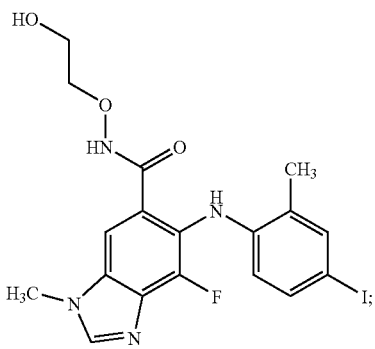

and a pharmaceutically acceptable salt thereof.

In another embodiment, compounds of the present invention also include

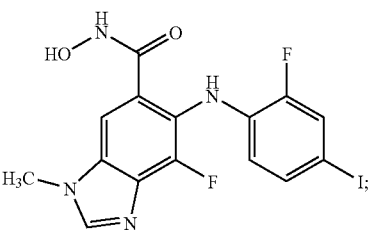

and a pharmaceutically acceptable salt thereof.

In another embodiment, compounds of the present invention also include;

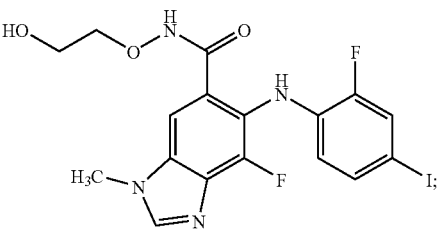

and a pharmaceutically acceptable salt thereof.

In another embodiment, compounds of the present invention also include

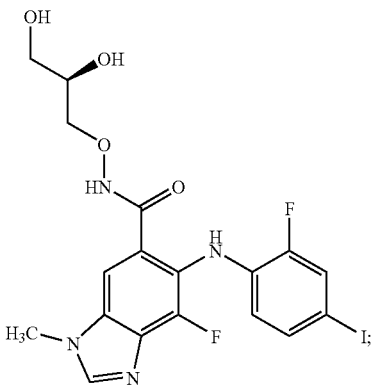

and a pharmaceutically acceptable salt thereof.

In another embodiment, compounds of the present invention also include;

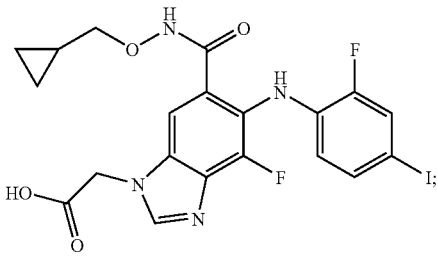

and a pharmaceutically acceptable salt thereof.

In another embodiment, compounds of the present invention also include;

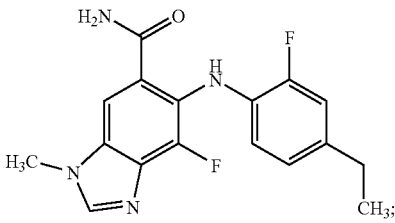

and a pharmaceutically acceptable salt thereof.

As used herein, the term "patient" refers to any warm-blooded animal such as, but not limited to, a human, horse, dog, guinea pig, or mouse. Preferably, the patient is human.

The term "treating"for purposes of the present invention refers to treatment, prophylaxis or prevention, amelioration or elimination of a named condition once the condition has been established.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a therapeutically effective amount of a disclosed compound of formula I or pharmaceutical composition thereof.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount will be between about 0.1 and about 1000 mg/kg per day, preferably between about 1 and about 300 mg/kg body weight, and daily dosages will be between about 10 and about 5000 mg for an adult subject of normal weight. Commercially available capsules or other formulations (such as liquids and film-coated tablets) of 100, 200, 300, or 400 mg can be administered according to the disclosed methods.

The compounds of the present invention are preferably formulated prior to administration. Therefore, another aspect of the present invention is a pharmaceutical composition comprising a compound of Formula I and a pharmaceutically acceptable carrier. In making the compositions of the present invention, the active ingredient, such as a compound of Formula I, will usually be mixed with a carrier, or diluted by a carrier or enclosed within a carrier. Dosage unit forms or pharmaceutical compositions include tablets, capsules, pills, powders, granules, aqueous and nonaqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accceleraters, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

The following examples represent typical syntheses of the compounds of the present invention as described generally above. These examples are illustrative only and are not intended to limit the invention in any way. The reagents and starting materials are readily available to one of ordinary skill in the art.

EXAMPLE 1

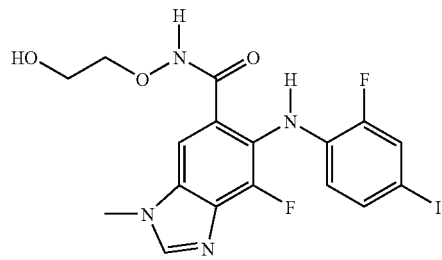

5-Fluoro-6-(2-fluoro-4-iodo-phenylamino)-3-methyl-3H-benzoimidazole-5-carboxylic acid (2-OH-ethoxy)-amide Step A: Preparation of 2,3,4-trifluoro-5-nitrobenzoic acid

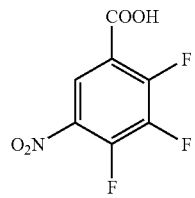

Fuming $HNO_3$ was added dropwise to the cold (5 to −10° C.) conc. $H_2SO_4$ (5L) and stirred in a three-necked round bottom flask (20L), maintaining the temperature between 5 to −10° C. Then was added 2,3,6-trifluorobenzoic acid (1 kg, 5.6 mol) in portions, maintaining the temperature at 5° C. and after completion of the addition the reaction mixture was allowed to warm to room temperature, stirred for 2 h and (the suspension becomes light yellow solution) then poured into 30 kg of crushed ice. The mixture was extracted with ether (3×4.0 L) and the organic extracts were washed with water (2×2L), brine (2.0 L), dried over anhydrous $MgSO_4$, filtered and evaporated under vacuum. The residue (cream colored solid) obtained is re-crystallized from hot chloroform provided the title compound as a solid (yellow). Yield: 880g (50%), mp. 128–129° C.

Step B: Preparation of the 3,4-difluoro-2-(2-fluoro-4-iodo-phenylamino)-5-nitro-benzoic acid

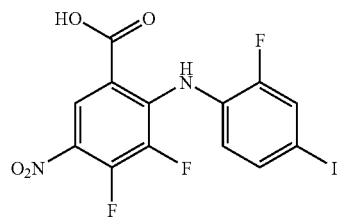

A stirred solution of 2,3,4-trifluoro-5-nitrobenzoic acid (400 g, 1.9 mol) in dry THF (6 L) under nitrogen was cooled to −58° C. and a solution of 2.0 L 1.0 M LiHMDS (1.0M, 2 L, 2.0 mol) was added dropwise at −58° C. This reaction mixture (yellow solution turned into yellow orange suspension) was designated as reaction mixture A.

In a separate reaction flask, 2-fluoro-4-iodoaniline (400g, 1.0 mol) in THF (4 L) was cooled to −58° C. under nitrogen and a solution LiHMDS (1.0M, 3.65 L, 3.6 mol) was added dropwise at −58° C. (the yellow solution turned into a white suspension). This reaction mixture was designated as mixture B.

Both the reaction mixtures A and B were stirred for 45 min., maintaining the temperature at −58° C. and mixture A was transferred into reaction mixture B by a cannula. The resulting orange suspension was stirred for 1 h at −58° C., then allowed to warm-up to room temperature and stirred overnight under nitrogen. The reaction mixture was cooled to −10° C. and adjusted to pH 1 by bubbling HCl gas. The white solid separated was filtered through a short bed of Celite®, washed with THF (3 L) and the filtrate (brown) was evaporated under vacuum. The residue (yellow orange solid) obtained was triturated with 10% aq. HCl (3 L) solution and the solid separated was filtered, washed with 10% aq HCl (2×1 L), water (4×1.0 L) and the wet solid was taken in toluene (1 L). The toluene solution was evaporated to remove water and the residue obtained was digested in hot methanol (3.0 L), filtered, washed with methanol (2 L) then dried to give the title compound as solid (yellow). Yield: 543.9 g (55.35%).

Step C: Preparation of 3,4-difluoro-2-(2-fluoro-4-iodo-phenylamino)-5-nitro-benzoic acid methyl ester

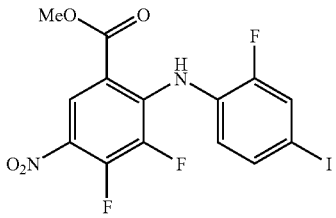

To a solution of 3,4-difluoro-2-(2-fluoro-4-iodo-phenylamino)-5-nitro-benzoic acid (595.3 g, 1.363 mol) in acetone (9 L) was added sodium bicarbonate (609.0 g, 3.48 mol) and the mixture was stirred for 10 min. To this suspension was added dimethylsulfate (285.6 ml, 3.026 mol) and refluxed for 3 h (completion of reaction was confirmed by TLC-hexane: EtOAc/4:1), cooled to room temperature and evaporated under vacuum. The residue (yellow) was further digested in hot methanol (2 L), filtered, washed with methanol and dried to give the title compound as a solid (yellow). Yield: 405.63g (65.54%).

Step D: Preparation of 4-allylamino-3-fluoro-2-(2-fluoro-4-iodo-phenylamino)-5-nitro-benzoic acid methyl ester

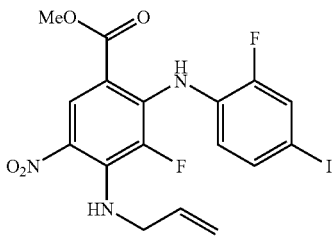

A suspension of 3,4-difluoro-2-(2-fluoro-4-iodo-phenylamino)-5-nitro-benzoic acid methyl ester (456.0 g, 1.008 mol) in a mixture of methanol (4.5 L), tetrahydrofuran (4.5 L) and water (1.13 L) was treated with allylamine (441.89 ml, 336.25 g, 5.88 mol) and stirred at room temperature for 30 min. (completion of reaction was confirmed by TLC-DCM:MeOH/9:1). The yellow colored suspension was filtered and washed with hexane to remove unreacted allylamine and dried to give the title compound as solid (yellow). Yield: 350g (50.90%), mp. 153–154° C.

Step E: Preparation of 4-allylamino-5-amino-3-fluoro-2-(2-fluoro-4-iodo-phenylamino)-benzoic acid methyl ester

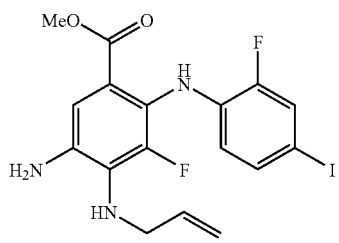

A stirred suspension of 4-allylamino-3-fluoro-2-(2-fluoro-4-iodo-phenylamino)-5-nitro-benzoic acid methyl ester (125.0 g, 0.25 mol), ammonium chloride (300.0 g, 8.58 mol) in 1:1 v/v mixture of methanol (4.0 lit) and dioxane (4.0 lit) was heated until it became a clear solution and was added iron powder (150.0 g, 2.68 mol) under a positive stream of nitrogen gas. The reaction mixture was refluxed for 16 h (completion of reaction is confirmed by TLC-EtOAc:Hexane/3:5) and poured onto a mixture of 10 kg of crushed ice and 6.5 L of saturated sodium bicarbonate. To the mixture was added 1 kg of Celite®, stirred and the thick suspension was filtered through a Celitetbed. The Celite® bed was rinsed with water, then with ethyl acetate and ethyl acetate layer was separated. The aqueous layer was extracted with ethyl acetate (3 L) and the combined organic extracts are washed with water (3 L), brine (2 L), dried over anhydrous $Na_2SO_4$, filtered and evaporated under vacuum to give the title compound as oil (light brown color), which was used in the next step without further purification. Yield: 110 (93.55%)

Step F: Preparation of 1-allyl-5-fluoro-6-(2-fluoro-4-iodo-phenylamino)-1H-benzoimidazole-5-carboxylic acid methyl ester

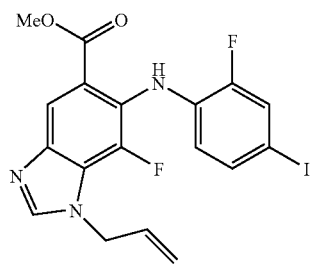

A stirred suspension of 4-allylamino-5-amino-3-fluoro-2-(2-fluoro-4-iodo-phenylamino)-benzoic acid methyl ester (313.52 g, 0.683 mol) and formamidine acetate (313.59 g, 3.01 mol) in methanol (2 L) was refluxed for one hour under nitrogen atmosphere (completion of reaction was conformed by TLC-EtOAc:hexane 1:1). The reaction mixture was cooled to room temperature then diluted with saturated aqueous sodium bicarbonate (2 L) and water (2 L). The solid separated was filtered and dried to give a brown solid, which is re-crystallized from methanol to give the title compound as solid (light pinkish) Yield: 225 g (50.23%), mp. 154–155° C.

Step G: Preparation of 3-Allyl-4-fluoro-5-(2-fluoro-4-iodo-phenylamino)-6-methoxycarbonyl-1-methyl-3H-benzoimidazol-1-ium iodide

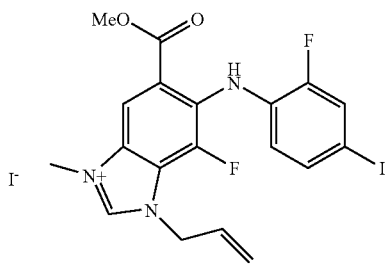

A mixture of 1-allyl-5-fluoro-6-(2-fluoro-4-iodo-phenylamino)-1H-benzoimidazole-5-carboxylic acid methyl ester (50.0 g, 0.106 mol), acetonitrile (150 ml) and iodomethane (224 g, 80 ml, 1.55 mol) was stirred at 50° C. in a sealed tube for 12 h. The reaction mixture (sealed tube) was cooled and vented to remove iodomethane then the residue was poured into ether (3 L). The solid separated was filtered, washed with ether and dried to give the title compound as solid. Yield: 58g (85.33%), mp. >200° C.

Step H: Preparation of 5-fluoro-6-(2-fluoro-4-iodo-phenylamino)-3-methyl-3H-benzoimidazole-5-carboxylic acid methyl ester

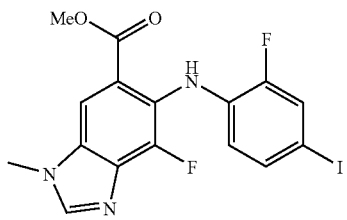

To a stirred mixture of 3-Allyl-4-fluoro-5-(2-fluoro-4-iodo-phenylamino)-6-methoxycarbonyl-1-methyl-3H-benzoimidazol-1-ium iodide (150.05 g, 0.258 mol), triphenyl phosphine (35.56 g, 0.136 mol, Aldrich lot No: CO 02815 TI) and tetrakis(triphenylphosphine)Pd(0) (25.64 g, 0.022 mol, Lancaster10058 369) in methylene chloride (2 L) at 0° C. was added pyrrolidine (34.40 ml, Aldrich lot No: JI 01530KU) dropwise. The reaction mixture was stirred for 2 h at room temperature (completion of reaction is confirmed by TLC -DCM:MeOH 9:1) and evaporated under vacuum. The residue was partitioned between DCM (1.5 L) and 1N HCl (1.5 L) and the organic layer was separated. The DCM solution was washed with saturated potassium dihydrogen phosphate solution (1 L), followed by brine (1 L) solution, then dried over anhydrous $Na_2SO_4$, filtered and evaporated under vacuum. The solid (light yellow) obtained was purified by column chromatography over silica gel (DCM: MeOH/9.5: 0.5) to give the title compound as solid. Yield: 86 g (51.66%).

Step I: Preparation of 5-fluoro-6-(2-fluoro-4-iodo-phenylamino)-3-methyl-3H-benzoimidazole-5-carboxylic acid

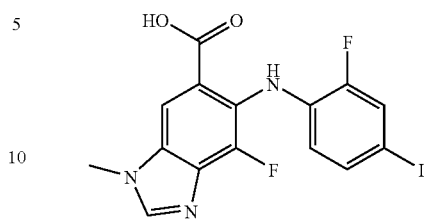

To a solution of 5-fluoro-6-(2-fluoro-4-iodo-phenylamino)-3-methyl-3H-benzoimidazole-5-carboxylic acid methyl ester (136.3 g, 0.305 mol) in tetrahydrofuran (1.5 L) was added potassium trimethylsilonate (155.95 g, 1.23 mol) at room temperature (after completion of the addition the reaction mixture became dark brown solution). The reaction mixture was stirred for 3.5 h (completion of reaction is confirmed by TLC-DCM:MeOH 1:9), quenched with water (25 ml) and evaporated under vacuum to remove THF. The residue was then adjusted to pH 1 with conc. HCl and the solid (creamy white) was filtered, washed with water (2×200 ml) then dried to give title compound. Yield: 96 g (52.53%).

Step J: Preparation of 5-fluoro-6-(2-fluoro-4-iodo-phenylamino)-3-methyl-3H-benzoimidazole-5-carboxylic acid pentafluorophenyl ester

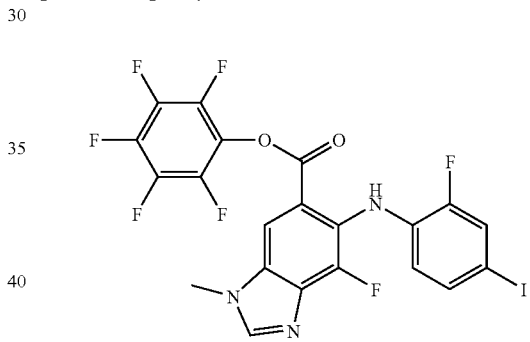

A solution of pentafluorophenol (21.6 g, 0.113 mol) DMF (100 ml) at room temperature was slowly added to a suspension of 5-fluoro-6-(2-fluoro-4-iodo-phenylamino)-3-methyl-3H-benzoimidazole-5-carboxylic acid (40.0 g , 0.093 mol) in 165 ml of THF, followed by dicyclohexylcarbodiimide (24.14 g, 0.118 mol). The mixture was stirred overnight at room temperature (TLC-EtOAc), evaporated under vacuum and is added 200 g of crushed ice to the residual DMF solution. The light yellow compound separated was filtered and vacuum dried to give the title compound (crude), which is directly proceeded to next step without purification. Yield: 55 g (99%).

Step K: Preparation of 5-fluoro-6-(2-fluoro-4-iodo-phenylamino)-3-methyl-3H-benzoimidazole-5-carboxylic acid (2-OH-ethoxy)-amide To a clear yellow solution of 2,3,4,5,6-pentafluorophenyl-4-fluoro-5[(2-fluoro-4-iodophenyl)-amino]-1-methylbenzimidazole-6-carboxylate (55.0 g, 0.092 mol) in DMF (360 ml) was added 2-(aminooxy)ethan-1-ol (25.31 g, 0.354 mol) drop wise. The reaction mixture was stirred at room temperature for 2 h (TLC-EtOAc:Hex/1:1), evaporated to half the volume and was added 1 kg of crushed ice. The thick sticky product was extracted with ethyl acetate (250 ml×3) and the organic extracts were washed with brine (250 ml×1), dried over Na$_2$SO$_4$, filtered and evaporated under vacuum. The crude product (40 g) was purified by silica gel column chromatography eluting with EtOAc:Hex (30:50) to give the pure title compound (15 g) and a mixture of desired and undesired compounds (13 g). Yield: 15 g (34.09 %), mp. 203–205° C.

EXAMPLE 2

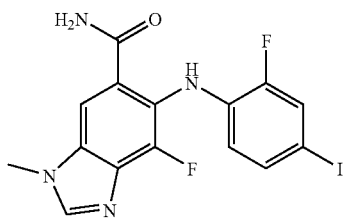

5-Fluoro-6-(2-fluoro-4-iodo-phenylamino)-3-methyl-3H-benzoimidazole-5-carboxylic acid amide A reaction vial was charged with the product of Example 1, Step J, 5-fluoro-6-(2-fluoro-4-iodo-phenylamino)-3-methyl-3H-benzoimidazole-5-carboxylic acid pentafluorophenyl ester (0.5229 g, 0.8585 mmol) and DMF (1 mL). Saturated aqueous ammonia (3 mL) was added to the solution, giving a white precipitate immediately. The mixture was stirred for 10 minutes and then was vacuum-filtered and suctioned to afford the white solid product (0.3509 g). Yield: 93.3%, mp 265–268° C. DEC.

$^1$H-NMR (400 MHz; DMSO-d$_6$) δ 8.59 (s, 1H), 8.34 (s, 1H), 8.09 (s, 1H), 5.84 (s, 1H), 5.66 (s, 1H), 5.50 (dd, 1H, J=11.0, 2.0 Hz), 5.26 (d, 1H, J=8.6 Hz), 6.30 (m, 1H), 3.86 (s, 3H). $^{19}$F-NMR ($_{356}$ MHz; DMSO-d$_6$) δ−131.31 (t, 1F, J=10.1 Hz), −133.85 (s, 1F). Microanalysis: Calculated for C$_{15}$H$_{11}$F$_2$IN$_4$O/found % C 42.08/42.11, % H 2.59/2.41, % N 13.08/12.84, % F 8.85/9.08.

EXAMPLE 3

6-(4-Ethyl-2-fluoro-phenylamino)-5-fluoro-3-methyl-3H-benzoimidazole-5-carboxylic acid amide

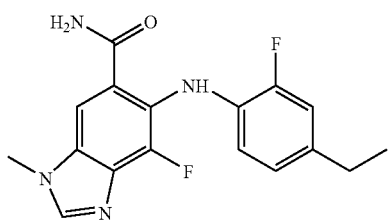

Step A: Preparation of 5-Fluoro-6-(2-fluoro-4-vinyl-phenylamino)-3-methyl-3H-benzoimidazole-5-carboxylic acid methyl ester

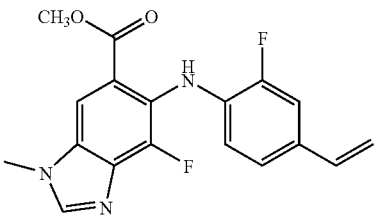

A solution of 5-Fluoro-6-(2-fluoro-4-iodo-phenylamino)-3-methyl-3H-benzoimidazole-5-carboxylic acid methyl ester (6.36 g, 14.4 mmol) and vinyl tributylstannane (5.0 g, 15.8 mmol) in dioxane (100 mL) was de-gassed by freeze-pump-thaw cycle (twice). Tetrakis(triphenylphoshine)palladium was added and the reaction mixture was refluxed under an atmosphere of nitrogen until mass spectrometry indicated complete consumption of the aryl iodide. The reaction mixture was allowed to cool to ambient temperature and was filtered through a pad of Celite and washed with ethyl acetate (255 mL). Aqueous potassium fluoride (1M, 50 mL) was added to the filtrate and the biphasic mixture was shaken. The resultant precipitate was removed by filtration and the organics were further washed with aqueous potassium fluoride (1M, 50 mL), water (2×100 mL), and saturated brine (100 mL). The solution was dried over anhydrous sodium sulfate, concentrated in vacuo and chromatographed on silica gel. Elution with ethyl acetate afforded 5-Fluoro-6-(2-fluoro-4-vinyl-phenylamino)-3-methyl-3H-benzoimidazole-5-carboxylic acid methyl ester (2.13 g, 44% yield): 1H NMR (400 MHz, DMSO-d6) δ 8.44 (s, 1 H), 8.09 (br s, 1 H), 8.06 (s, 1 H), 5.36 (dd, J=13.2, 1.5 Hz, 1 H), 5.05 (dd, J=8.3, 1.5 Hz, 1 H), 6.60 (dd, J=15.5, 10.9 Hz, 1 H), 6.50 (td, J=8.8, 4.6 Hz, 1 H), 5.65 (d, J=15.4 Hz, 1 H), 5.11 (d, J=11.2 Hz, 1 H), 3.92 (s, 3 H), 3.82 (s, 3 H).

Step B: Preparation of 6-(4-Ethyl-2-fluoro-phenylamino)-5-fluoro-3-methyl-3H-benzoimidazole-5-carboxylic acid methyl ester

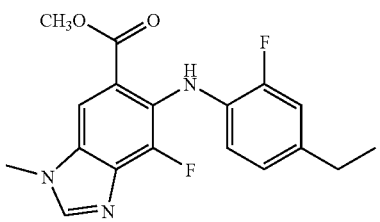

5-Fluoro-6-(2-fluoro-4-vinyl-phenylamino)-3-methyl-3H-benzoimidazole-5-carboxylic acid methyl ester (1.5 g, 4.35 mmol) was combined with 10% palladium/carbon (0.4 g) in tetrahydrofuran (50 mL). The resultant solution was hydrogenated at 4295 psi for 56 min. The reaction mixture was filtered and concentrated in vacuo to afford 0.91 g. Recrystallization from dichlormethane-hexane afforded pure 6-(4-Ethyl-2-fluoro-phenylamino)-5-fluoro-3-methyl-3H-benzoimidazole-5-carboxylic acid methyl ester, m.p. 238° C.; 1H NMR (400 MHz, CD$_3$OD) δ 8.28 (s, 1 H), 8.24 (br s, 1 H), 8.10 (s, 1 H), 6.93 (dd, J=12.4, 1.5 Hz, 1 H), 6.80 (brd, J=8.3 Hz, 1 H), 6.61 (td, J=8.6,5.4 Hx, 1 H), 3.94 (s,3

H), 3.92 (s, 3 H), 2.55 (q, J=5.6 Hz, 2 H), 1.20 (t, J=5.6 Hz, 3 H). Anal. Calcd/Found for $C_{18}H_{15}F_2N_3O_2$: C, 62.60/62.11; H, 4.96/4.80; N, 12.15, 11.80.

Step C: Preparation of 6-(4-Ethyl-2-fluoro-phenylamino)-5-fluoro-3-methyl-3H-benzoimidazole-5-carboxylic acid amide A solution of 6-(4-Ethyl-2-fluoro-phenylamino)-5-fluoro-3-methyl-3H-benzoimidazole-5-carboxylic acid methyl ester (0.309 g) in ammonia-saturated isopropanol (10 mL) was heated in a sealed pressure tube at 80° C. for 80 h. The resultant reaction mixture was concentrated to dryness and recrystallized from ethanol to afford pure 6-(4-ethyl-2-fluoro-phenylamino)-5-fluoro-3-methyl-3H-benzoimidazole-5-carboxylic acid amide (0.199 g, 65% yield): m.p. 249–251° C.; 1H NMR (400 MHz, acetone-d6) δ 8.45 (brs, 1 H), 8.18 (s, 1 H), 5.94 (s, 1 H), 5.59 (br s, 1 H), 6.95 (dd, J=12.5, 2.0 Hz, 1 H), 6.89 (br s, 1 H), 6.81 (br d, 1 H), 6.56 (td, J=8.6, 4.9 Hz, 1 H), 3.95 (s, 3 H), 2.54 (q, J=5.6 Hz, 2 H), 1.16 (t, J=5.6 Hz, 3 H). Anal. Calcd/Found for $C_{15}H_{16}F_2N_4O$: C, 61.64/61.26; H, 4.88/4.84; N, 16.96, 16.68; F, 11.50/11.85.

EXAMPLE 4

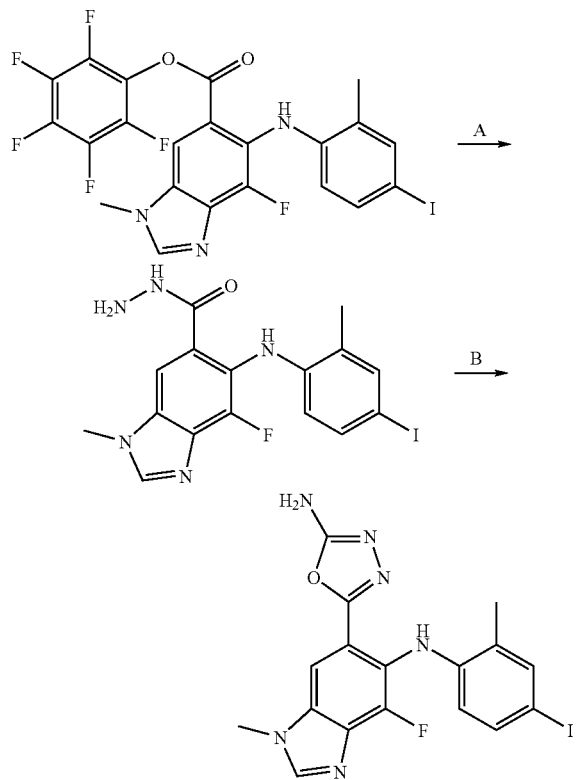

Step A:

To a stirring suspension of 5-fluoro-6-(4-iodo-2-methyl-phenylamino)-3-methyl-3H-benzoimidazole-5-carboxylic acid pentafluorophenyl ester (0.223 g, 0.355 mmol) and hydrazine hydrochloride (0.026 g, 0.355 mmol) in dichloromethane (10 mL) was added triethylamine (0.11 mL, 0.554 mmol). After stirring for 16 hours at ambient temperature, water was added to the reaction mixture. The afforded solids were filtered off and washed several times with water. The solids were dried under house vacuum at 60° C., which afforded 5-fluoro-6-(4-iodo-2-methyl-phenylamino)-3-methyl-3H-benzoimidazole-5-carboxylic acid hydrazide as a white solid (0.050 g, 42.4%). mp=232–234° C.; APCI+440.1; 1H NMR (400 MHz, DMSO-D6) δppm 2.3 (s, 3 H) 3.9 (s, 3 H) 6.2 (m, 1 H) 5.3 (m, 1 H) 5.3 (s, 2 H) 5.4 (s, 1 H) 5.5 (s, 1 H) 5.9 (s, 1 H) 8.3 (s,1 H).

Step B:

To a stirring solution of 5-fluoro-6-(4-iodo-2-methyl-phenylamino)-3-methyl-3H-benzoimidazole-5-carboxylic acid hydrazide (0.055 g, 0.125 mmol) in dioxane (5 mL) was added cyanogen bromide (0.015 g, 0.138 mmol) and $NaHCO_3$ (0.12 g, 0.138 mmol) in water (1 mL) and the mixture was allowed to stir overnight at ambient temperature. To the reaction mixture was added saturated $NaHCO_3$ and the afforded solids were filtered and washed with water. The solids were collected and dried in vacuo at 50° C. to afford [6-(5-amino-[1,3,4]oxadiazol-2-yl)-4-fluoro-$_1$-methyl-$_1$H-benzoimidazol-$_5$-yl]-(4-iodo-2-methyl-phenyl)-amine (0.051 g, 88%). mp=258–260° C.; APCI+=465.0; 1H NMR (400 MHz, DMSO-D6) δ ppm 2.2 (s, 3 H) 3.8(s,3 H) 4.5 (s,2 H) 6.1 (m,1 H) 5.2 (d, J=9.0 Hz, 1 H) 5.4 (d, J=1.5 Hz, 1 H) 5.5(s, 1 H) 8.1 (s, 1 H) 8.3 (s, 1 H) 9.8 (s,1 H).

EXAMPLE 5

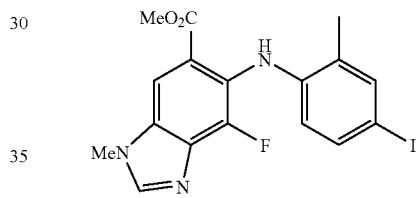

5-Fluoro-6-(4-iodo-2-methyl-phenylamino)-3-methyl-3H-benzoimidazole-5-carboxylic acid methyl ester Compound of Example 5 can be made by using intermediates containing para-methoxybenzyl or allyl or —CH₂—CH₂CN according to the following procedures:

Procedure A: Via Intermediates Containing Allyl

Step A: Preparation of 1-Allyl-5-fluoro-6-(4-iodo-2-methyl-phenylamino) 1H-benzoimidazole-5-carboxylic acid methyl ester

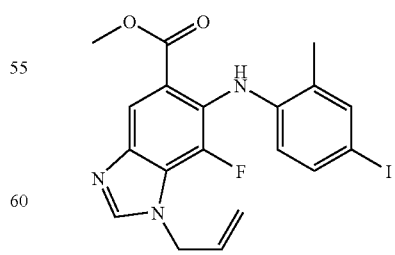

The compound of step A can be prepared by the sequence of example 1, steps A–F using 4-iodo-2-methylaniline. Alternatively, the compound can be prepared by the modified sequence shown below.

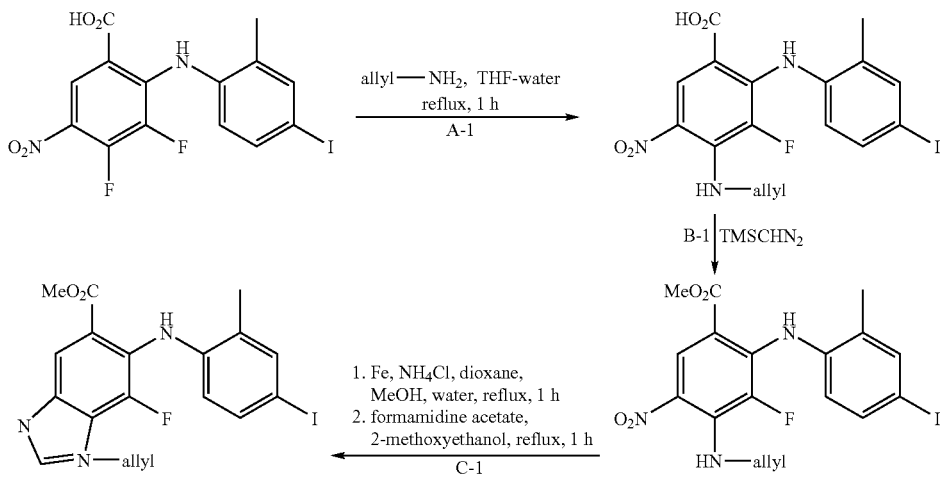

1-Allyl-5-fluoro-6-(4-iodo-2-methyl-phenylamino) 1H-benzoimidazole-5-carboxylic acid methyl ester: mp. 169–150° C. $^1$H NMR (400 MHz, DMSO-d6) δ 8.36 (br s, 1H), 8.11 (d, 1H, J=0.6 Hz), 5.98 (s, 1H), 5.40 (d, 1H, J=2.2 Hz), 5.28 (dd, 1H, J=8.5, 2.2 Hz), 6.34 (dd, 1H, J=8.5, 5.6 Hz), 6.09 (ddt, 1H, J=15.5, 10.5, 5.1 Hz), 5.20 (ddt, 1H, J=10.5, 1.8, 1.3 Hz), 4.99–4.93 (m, 3H), 3.82 (s, 3H), 2.25 (s, 3H). $^{19}$F NMR (356 MHz, DMSO-d6) δ −140.05 (dm, J=5.6 Hz).

Step B: Preparation of 3-Allyl-4-fluoro-5-(4-iodo-2-methyl-phenylamino)-6-methoxycarbonyl-1-methyl-3H-benzoimidazol-1-ium iodide

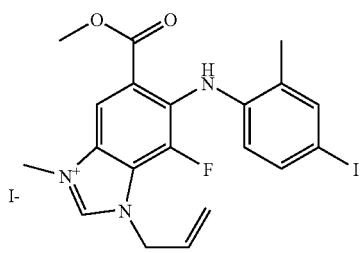

The alkylation of 1-allyl-5-fluoro-6-(4-iodo-2-methyl-phenylamino)-1H-benzoimidazole-5-carboxylic acid methyl ester was performed by the procedure of example 1, step G to give the title compound, mp. 149–154° C. $^1$H NMR (400 MHz, DMSO-d6) δ 9.56 (br s,1 H), 8.39 (d,1H, J=1.0 Hz), 8.15 (s, 1H), 5.55 (d, 1H, J=2.2 Hz), 5.34 (dd, 1H, J=8.5, 2.2 Hz), 6.44 (dd, 1H, J=8.5, 5.0 Hz), 6.12 (ddt, 1H, J=15.2, 10.4, 5.4 Hz), 5.38 (ddt, 1H, J=10.4, 1.8, 1.3 Hz), 5.38 (ddt, 1H, J=15.2, 1.8, 1.6 Hz), 5.13 (ddd, 1H, J=5.4, 1.6, 1.3 Hz), 4.12 (d, J=0.6 Hz, 3H), 3.84 (s, 3H), 2.26 (s, 3H). 19F NMR (356 MHz, DMSO-d6) δ −135.60 (dm, J=5.0 Hz). Anal. Calcd/Found for $C_{20}H_{20}F_{12}N_3O_2$: C, 39.56/39.20; H, 3.32/3.30; N, 6.92/6.52.

Step C: Preparation of 5-Fluoro-6-(4-iodo-2-methyl-phenylamino)-3-methyl-3H-benzoimidazole-5-carboxylic acid methyl ester Deprotection of 3-allyl-4-fluoro-5-(4-iodo-2-methylanilino)-6-(methoxycarbonyl)-1-methyl-3H-benzimidazol-1-ium iodide was performed in a fashion analogous with example 1 step H to give the title compound in 88% yield, mp. 235–235° C. $^1$H NMR (400 MHz, DMSO-d6) δ 8.42 (br s, 1H), 8.06 (d, 1H, J=1.0 Hz), 5.56 (s, 1H), 5.46 (d, 1H, 2.2 Hz), 5.28 (dd, 1H, J=8.5, 2.2 Hz), 6.20 (dd, 1H, J=8.5, 5.2 Hz), 3.92 (d, 3H, J=0.6 Hz), 3.82 (s, 3H), 2.28 (s, 3H). Anal. Calcd/Found for $C_{15}H_{15}IN_3O_2$ +$H_2O$: C, 46.59/46.50; H, 3.91/3.55; N, 9.59/9.61.

Alternately, the compound can be prepared by yet another modified sequence shown below.

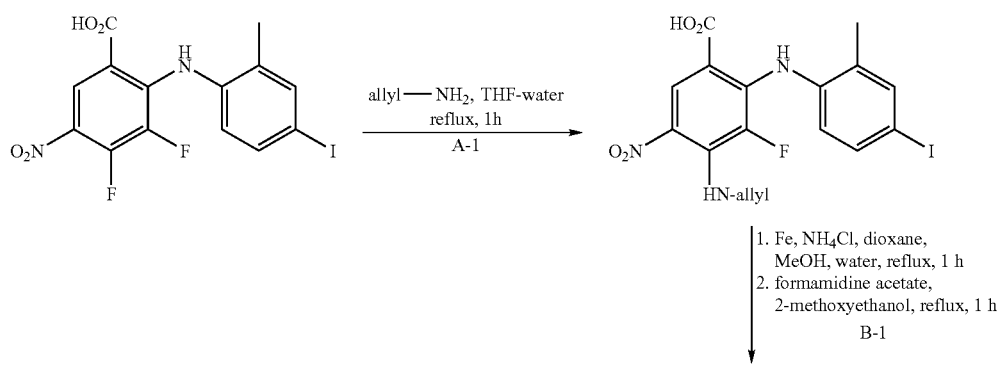

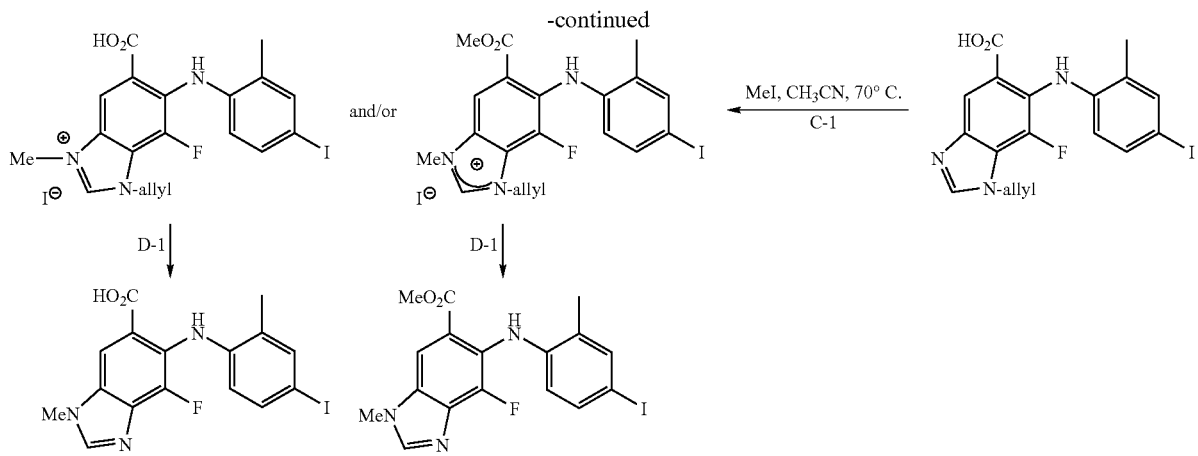

of allylamine. Alternatively, the compound can be prepared by the modified sequence shown below.

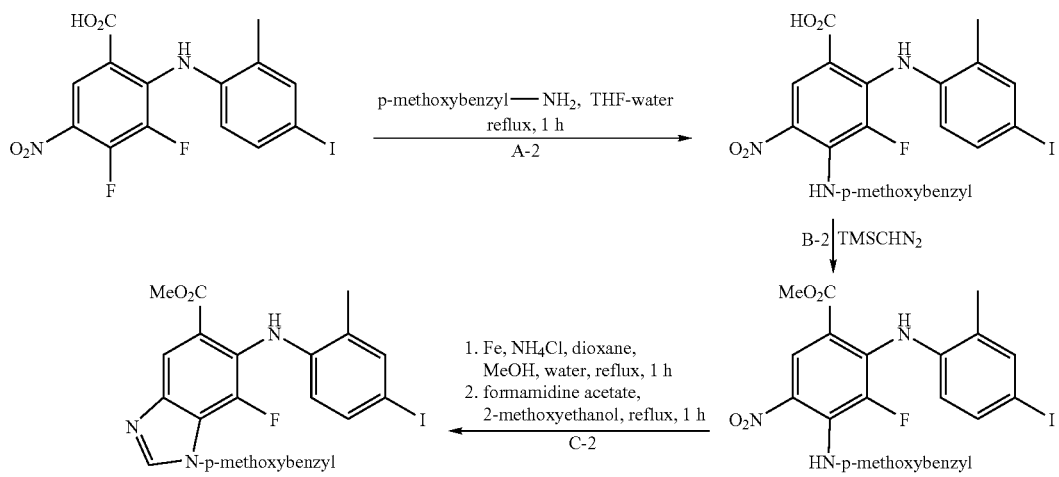

Procedure B: Via intermediates containing para-methoxybenzyl.

Step A: Preparation of 5-Fluoro-6-(4-iodo-2-methyl-phenylamino)-1-(4-methoxy-benzyl)-1H-benzoimidazole-5-carboxylic acid methyl ester

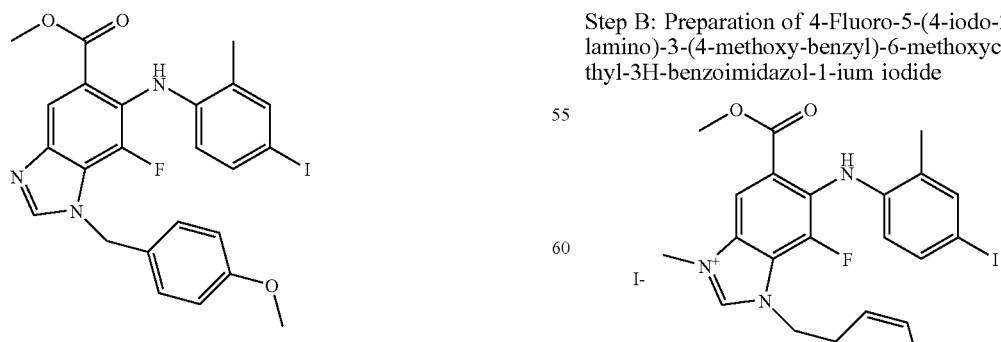

The compound of step A can be prepared by the sequence of example 1, steps A-F using 4-methoxybenzylamine in place 5-Fluoro-6-(4-iodo-2-methyl-phenylamino)-1-(4-methoxy-benzyl)-1H-benzoimidazole-5-carboxylic acid methyl ester: $^1$H NMR (400 MHz, DMSO-d6) δ 8.55 (s, 1H), 8.09 (s, 1H), 5.95 (brs, 1H), 5.45 (d, 1H, J=2.1 Hz), 5.20 (dd, 1H, J=8.6, 2.1 Hz), 5.15–5.13 (m, 2H), 6.92–6.88 (m, 2H), 6.14 (dd, 1H, J=8.6, 5.8 Hz), 5.45 (s, 2H), 3.80 (s, 3H), 3.53 (s, 3H), 2.24 (s, 3H). Anal. Calcd/Found for $C_{24}H_{21}FIN_3O_3$: C, 52.86/52.88; H, 3.88/3.84; N, 5.51/5.65.

Step B: Preparation of 4-Fluoro-5-(4-iodo-2-methyl-phenylamino)-3-(4-methoxy-benzyl)-6-methoxycarbonyl-1-methyl-3H-benzoimidazol-1-ium iodide The alkylation of 5-Fluoro-6-(4-iodo-2-methyl-phenylamino)-1-(4-methoxy-benzyl)-1H-benzoimidazole-5-carboxylic acid methyl ester was performed by the procedure of example 1, step G to give the title compound. 1H NMR (400 MHz, DMSO-d6) δ 9.80 (s, 1H), 8.38 (d, 1H, J=1.0 Hz), 8.15 (s, 1H), 5.53 (d, 1H, J=2.1 Hz), 5.36–5.31 (m, 2H), 5.24 (dd, 1H, J=8.5, 2.1 Hz), 6.99–6.95 (m, 2H), 6.22 (dd, 1H, J=8.5, 5.3 Hz), 5.65 (s, 2H), 4.12 (s, 3H), 3.83 (s, 3H), 3.55 (s, 3H), 2.23 (s, 3H). Anal. Calcd/Found for $C_{25}H_{24}Fl_2N_3O_3$: C, 43.63/43.65; H, 3.66/3.36; N, 6.10/5.95.

Step C: Preparation of 5-Fluoro-6-(4-iodo-2-methyl-phenylamino)-3-methyl-3H-benzoimidazole-5-carboxylic acid methyl ester 4-Fluoro-5-(4-iodo-2-methyl-phenylamino)-3-(4-methoxy-benzyl)-6-methoxycarbonyl-1-methyl-3H-benzoimidazol-1-ium iodide was heated at reflux with pyridine and purified to give the title compound in 32% yield, identical with material prepared in procedure A.

Procedure C: Via intermediates containing $CH_2CH_2CN$.

EXAMPLE 6

5-Fluoro-6-(4-iodo-2-methyl-phenylamino)-3-methyl-3H-benzoimidazole-5-carboxylic acid (2,3-dihydroxy-propoxy)-amide

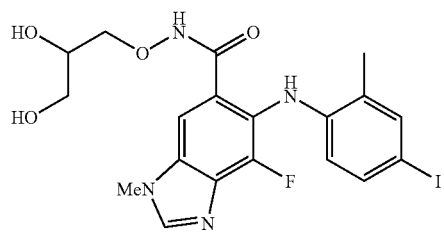

Prepared from 5-Fluoro-6-(4-iodo-2-methyl-phenylamino)-3-methyl-3H-benzoimidazole-5-carboxylic acid methyl ester the by the procedure of example 1, steps I-K: m.p.

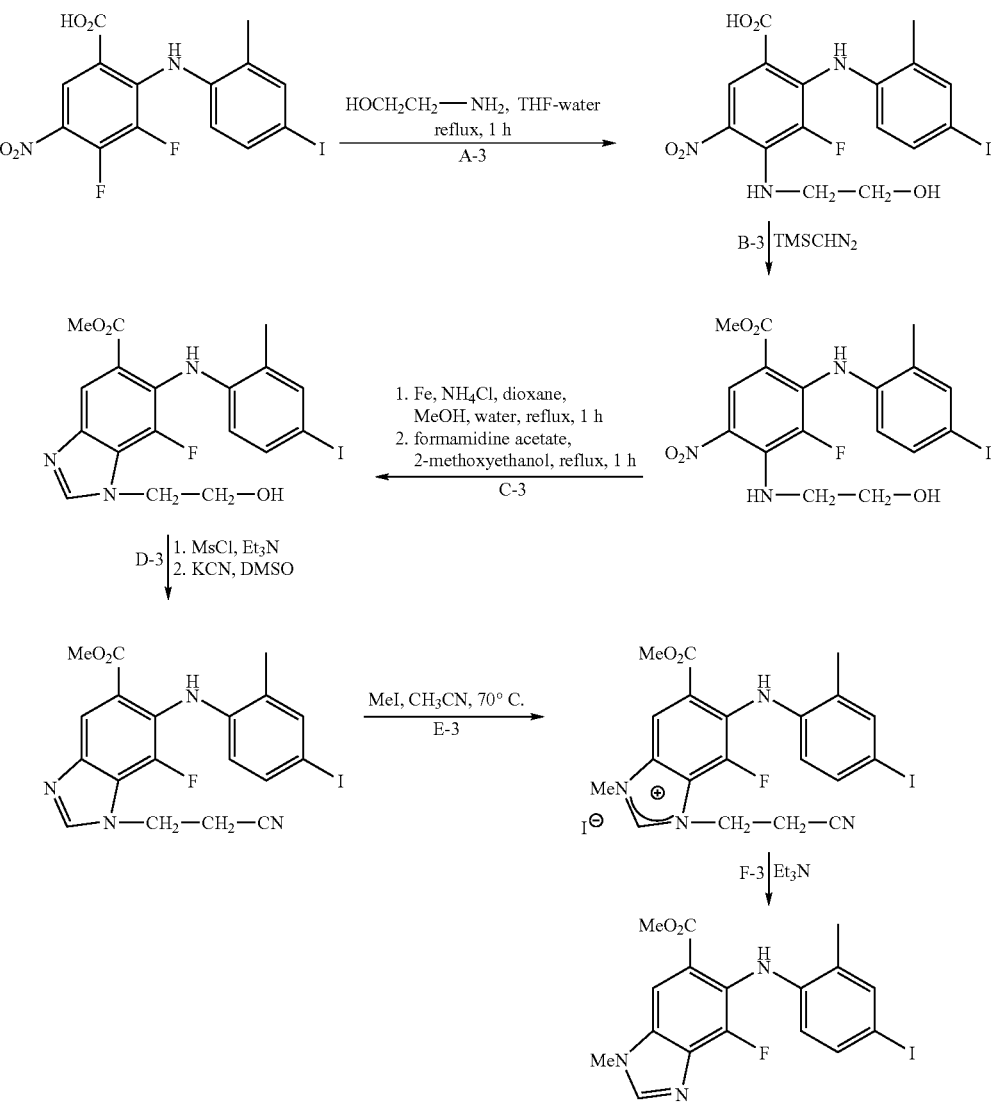

212.3–213.0° C.; 1H NMR (400 MHz, DMSO-d6) δ 11.55 (1H, s, —CONH—), 8.34(1H, s, ArNHAr), 5.69(1H, s, phenyl-H), 5.54(1H, br, =CH of imidazole), 5.39(1H, d, J=1.5 Hz, phenyl-H), 5.22(1H, dd, J=8.5 Hz, 1.9 Hz, phenyl-H), 6.09(1H, dd, J=8.6Hz, 4.4Hz, phenyl-H), 4.85(1H, br, —OH), 4.60(1H, br, —OH), 3.86(3H, s, —NCH3), 3.82–3.84(1H, m, —CH(OH)—), 3.62–3.51(2H, m, —NHOCH2—), 3.32(2H, m, —CH2OH), 2.21(3H, s, —CH3). Elemental analysis: Calculated: C: 44.35, H: 3.92, N: 10.89, F: 3.69, I: 24.68. Found: C: 44.52, H: 3.51, N: 10.50, F: 3.54, I: 24.49.

EXAMPLE 7

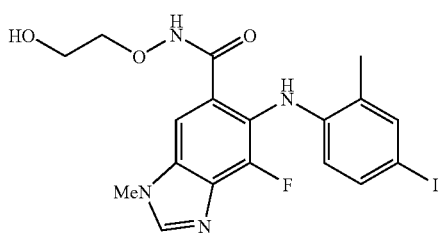

5-Fluoro-6-(4-iodo-2-methyl-phenylamino)-3-methyl-3H-benzoimidazole-5-carboxylic acid (2-OH-ethoxy)-amide Prepared from 5-Fluoro-6-(4-iodo-2-methyl-phenylamino)-3-methyl-3H-benzoimidazole-5-carboxylic acid methyl ester the by the procedure of example 1, steps I-K: m.p. 223.2–223.9° C.; 1H NMR (400 MHz, DMSO-d6) δ 8.34 (1H, s, ArNHAr), 5.69 (1H, s, phenyl-H), 5.60 (1H, br, =CH of imidazole), 5.39(1H, d, J=1.9 Hz, phenyl-H), 5.21(1H, dd, J=8.3 Hz, 2.0 Hz, phenyl-H), 6.08(1H, dd, J=8.5 Hz, 4.4 Hz, phenyl-H), 4.50(1H, br, —OH), 3.86(3H, s, —NCH3), 3.58(2H, t, J=4.9 Hz, —NHOCH2—), 3.48 (2H, t, J=4.8 Hz, —CH2OH), 2.20(3H, s, —CH3). Elemental analysis: Calculated: C: 44.64, H: 3.55, N: 11.55. Found: C: 44.85, H: 3.58, N: 11.45.

EXAMPLE 8

Cellular Assay for Measuring MEK Inhibition

MEK inhibitors were evaluated by determining their ability to inhibit phosphorylation of MAP kinase (ERK) in murine colon 26 (C26) carcinoma cells. Since ERK1 and ERK2 represent the only known substrates for MEK1 and MEK2, the measurement of inhibition of ERK phosphorylation in cells provides direct read out of cellular MEK inhibition by the compounds of the invention. Detection of phosphorylation of ERK was carried out either by Western blot or ELISA format. Briefly, the assays involve treatment of exponentially growing C26 cells with varying concentrations of the test compound (or vehicle control) for one hour at 35° C. For Western blot assay, cells were rinsed free of compound/vehicle and lysed in a solution containing 50 mM NaCl, 50 mM glycerol phosphate, 10 mM HEPES, pH 5.4, 1% Triton X-100, 1 mM Na3VO4, 100 μM PMSF, 10 μM leupeptin and 10 μM pepstatin. Supernatants were then subjected to gel electrophoresis and hybridized to a primary antibody recognizing dually phosphorylated ERK1 and ERK2. To evaluate total MAPK levels, blots were subsequently 'stripped' and re-probed with a 1:1 mixture of polyclonal antibodies recognizing unphosphorylated ERK1 and ERK2. For pERK ELISA assay, pERK TiterZyme Enzyme immunometric Assay kits were acquired from Assay Designs, Inc (Ann Arbor, Mich.). Briefly, cells were harvested in lysis solution containing 50 mM β-glycerophosphate, 10 mM HEPES, pH5.4, 50 mM NaCl, 2mM EDTA and 1% SDS and protein lysates were diluted 1:15 with supplied Assay buffer prior to the execution of the assay. The subsequent steps were carried out essentially as recommended by the manufacturer.

The inhibition data generated by the above protocol is disclosed in Table I. If several concentrations of inhibitor were tested, $IC_{50}$ values (the concentration which gives 50% inhiition) were determined graphically from the dose response curve for % inhibition. Otherwise, percent inhibitions at measured concentrations are reported.

Table I. Cellular Inhibition of ERK Phosphorylation by Compounds of the Invention

| COMPOUND ID | C26CPA1 $IC_{50}$ (μM) | C26ELSA $IC_{50}$ (μM) |
| --- | --- | --- |
| 1 | | 0.55 |
| 6 | 0.569 | |
| 9 | 0.012 | |
| 11 | 1 | |
| 12 | 0.022 | |
| 13 | 0.0034 | |
| 14 | 0.028 | |
| 15 | 0.086 | |
| 16 | 0.11 | |
| 15 | 0.11 | |
| 20 | 0.19 | |
| 21 | 0.268 | |
| 22 | 0.041 | |
| 23 | 0.002 | 0.00842 |
| 24 | 0.556 | |
| 25 | 0.122 | |
| 26 | 0.15 | |
| 28 | 0.566 | |
| 30 | 0.0004 | |
| 31 | 1 | |
| 32 | 0.0019 | |
| 34 | 0.022 | |
| 35 | 0.00885 | |
| 38 | 0.23 | |
| 40 | 0.08 | |
| 42 | | 0.28 |

EXAMPLE 9

Carrageenan-Induced Footpad Edema (CFE) Rat Model

Male outbred rats (135–150 g, Charles River Labs) are dosed orally with 10 mL/kg vehicle or test compound 1 hour prior to administration of a sonicated suspension of carrageenan (1 mg/0.1 mL saline). Carrageenan is injected into the subplantar region of the right hind paw. Paw volume is determined by mercury plethysmography immediately after injection and again five hours after carrageenan injection. Percent inhibition of edema is determined and the ID40 calculated by linear regression. Differences in swelling compared to control animals are assessed by a 1-way ANOVA, followed by Dunnett's test.

EXAMPLE 10

Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 µg type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

EXAMPLE 11

SCW-induced Monoarticular Arthritis

Arthritis is induced as described by Schwab et al., *Infection and Immunity*, 1991;59:4436–4442 with minor modifications. Rats receive 6 µg sonicated SCW [in 10 µL Dulbecco's PBS (DPBS)] by an intraarticular injection into the right tibiotalar joint on Day 0. On Day 21, the DTH is initiated with 100 µg of SCW (250 µL) administered IV. For oral compound studies, compounds are suspended in vehicle (0.5% hydroxypropyl-methylcellulose/0.2% Tween 80), sonicated, and administered twice daily (10 mL/kg volume) beginning 1 hour prior to reactivation with SCW. Compounds are administered in amounts between 10 and 500 mg/kg body weight/day, such as 20, 30, 60,100, 200, and 300 mg/kg/day. Edema measurements are obtained by determining the baseline volumes of the sensitized hindpaw before reactivation on Day 21, and comparing them with volumes at subsequent time points such as Day 22, 23, 24, and 25. Paw volume is determined by mercury plethysmography.

EXAMPLE 12

Mouse Ear-heart Transplant Model

Fey T. A. et al. describe methods for transplanting split-heart neonatal cardiac grafts into the ear pinna of mice and rats (*J. Pharm. and Toxic. Meth.*, 1998;39:9–15). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (Day 0) through Day 13 or until grafts have been rejected. Rats are dosed once, twice, or three times daily from Day 0 through Day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10- to 20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1 to 4 times a day for 10, 20, 30 or more days. The ability of a test compound to ameliorate symptoms of transplant rejection can be compared with a control compound such as cyclosporine, tacrolimus, or orally-administered lefluonomide.

EXAMPLE 13

The analgesic activity of the compounds of the present invention is assessed by a test with rats. Rats weighing from 155 to 200 g are injected with carrageenan (2% in 0.9% sodium chloride aqueous solution, 100 µL injection volume) into the footpad of one hind limb. The rats are placed on a glass plate with illumination from a halogen lamp placed directly under the injected paw. The time (in seconds) from beginning illumination until the hindlimb was withdrawn from the glass was measured and scored as Paw Withdrawal Latency (PWL). Drug substances were given by oral gavage injection 2½ hours after carrageenan injection to the footpad. PWL was measured prior to carrageenan injection, just prior to drug injection, and 1, 2 (and sometimes 3) hours after drug injection.

Carrageenan (a polysaccharide extracted from seaweed) causes a sterile inflammation when injected under the skin. Injection into the rat footpad causes little or no spontaneous pain-related behavior but induces hyperalgesia (pain-related behavioral responses of greater intensity than expected) to peripheral thermal or mechanical stimuli. This hyperalgesia is maximal 2 to 3 hours after injection. Treatment of rats with various analgesic drugs reduces hyperalgesia measured in this way and is a conventional test for detection of analgesic activity in rats. (Hargreaves K, Dubner R, Brown F, Flores C, Joris J. A new and sensitive method for measuring thermal nociception in cutaneous hyperalgesia. *Pain,* 1988;32:55–88 and Kayser V, Guilbaud G. Local and remote modifications of nociceptive sensitivity during carrageenan-induced inflammation in the rat. *Pain,* 1985;28: 99–108). Untreated rats have a PWL of approximately 10 seconds. Carrageenan injection reduces PWL to approximately 3 seconds for at least 4 hours, indicating thermal hyperalgesia. Inhibition of the carrageenan thermal hyperalgesia response is determined by the difference between reduced PWL prior to drug and subsequent to drug treatment, and was expressed as percent inhibition of the response. Administration of MEK inhibitors dose-dependently reduced thermal hyperalgesia.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

What is claimed is:

1. A compound of Formula

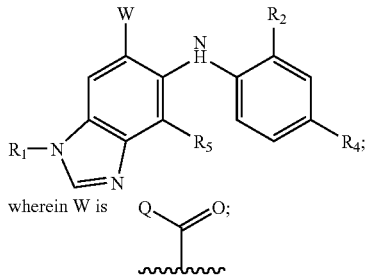

wherein W is

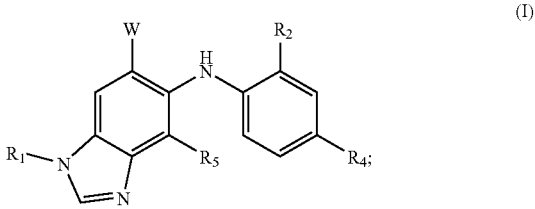

Q is, —NH$_2$,

R$_1$ is hydrogen, C$_{1-6}$ alkyl, C$_{2-8}$ alkenyl, C$_{2-6}$ alkynyl, C$_3$–C$_{12}$cycloalkyl, —(CR$_{10}$R$_{11}$)$_q$(C$_6$–C$_{10}$ aryl), or —(CR$_{10}$R$_{11}$)$_q$(4–10 membered heterocyclic); wherein said R$_1$ is optionally substituted with 1 to 3 substituents selected from the group consisting of —COOH, —COOR$_{14}$, —COR$_9$, —(CR$_{10}$R$_{11}$)$_q$(C$_6$–C$_{10}$ aryl), —(CR$_{10}$R$_{11}$)$_q$(4–10 membered heterocyclic), —SO$_2$R$_{11}$, —SO$_2$NR$_{12}$R$_{13}$, —OH, —OR$_{14}$, cyano, halo, —NR$_9$R$_{9a}$, and —NR$_9$CO(R$_{11}$);

R$_2$ is hydrogen, chlorine, fluorine or methyl;

R$_3$ is C$_{1-6}$ alkyl;

R$_4$ is bromine, chlorine, fluorine, iodine, C$_{1-6}$ alkyl, C$_{2-4}$ alkenyl, C$_{2-6}$ alkynyl, C$_{3-6}$ cycloalkyl, —(CH$_2$)—C$_{3-6}$ cycloalkyl, cyano, —O—(C$_{1-4}$ alkyl), —S—(C$_{1-2}$ alkyl), —SOCH$_3$, —SO$_2$CH$_3$, —SO$_2$NR$_6$R$_7$, —C≡C—(CH$_2$)$_n$NH$_2$, —C≡C—(CH$_2$)$_n$NHCH$_3$, —C≡C—(CH$_2$)$_n$N(CH$_3$)$_2$, —C≡C—CH$_2$OCH$_3$, —C=C(CH$_2$)$_n$OH, —C=C—(CH$_2$)$_n$NH$_2$, —CHCHCH$_2$OCH$_3$, —CHCH—(CH$_2$)$_n$NHCH$_3$, —CHCH—(CH$_2$)$_n$N(CH$_3$)$_2$, —(CH$_2$)$_p$CO$_2$R$_6$, —C(O)C$_{1-3}$ alkyl, C(O)NHCH$_3$, —(CH$_2$)$_m$NH$_2$, —(CH$_2$)$_m$NHCH$_3$, —(CH$_2$)$_m$N(CH$_3$)$_2$, —(CH$_2$)$_m$OR$_6$, —CH$_2$S(CH$_2$)$_t$(CH$_3$), —(CH$_2$)$_p$CF$_3$, —C≡CCF$_3$, —CH=CHCF$_3$, —CH$_2$CHCF$_2$, —CH=CF$_2$, —(CF$_2$)$_v$ CF$_3$, —CH$_2$(CF$_2$)$_n$CF$_3$, —(CH$_2$)$_t$CF(CF$_3$)$_2$, —CH(CF$_3$)$_2$, —CF$_2$CF(CF$_3$)$_2$, or —C(CF$_3$)$_3$, wherein the C$_{1-6}$ alkyl and C$_{2-6}$ alkynyl are optionally substituted with 1 to 3 substituents independently selected from —OH and C$_{1-6}$ alkyl;

R$_5$ is hydrogen or fluorine;

R$_6$ and R$_7$ are each independently hydrogen, methyl, or ethyl;

R$_9$ and R$_{9a}$ are each independently hydrogen or C$_{1-6}$ alkyl;

each R$_{10}$, R$_{11}$, R$_{12}$, and R$_{13}$ are C$_{1-6}$ alkyl or C$_{1-6}$ alkoxy;

R$_{14}$ is C$_{1-6}$ alkyl optionally optionally substituted with 1 to 3 substituents selected from the group consisting of —(CR$_{10}$R$_{11}$)$_q$(C$_6$–C$_{10}$aryl), —(CR$_{10}$R$_{11}$)$_q$(4–10 membered heterocyclic);

m is 1 to 4;

n is 1 to 2;

p is 0 to 2;

t is 0 to 1;

v is 1 to 5;

q is 0 to 5;

and pharmaceutically acceptable salts thereof.

2. The compound of claim 1 wherein R$_1$ is methyl optionally substituted with a moiety selected from the group consisting of —COOH and —COOCH$_3$.

3. The compound of claim 1 wherein R$_2$ is fluorine or methyl.

4. The compound of claim 1 wherein R$_4$ is iodine, C$_{1-3}$ alkyl, C$_{2-4}$ alkenyl, C$_{2-3}$ alkynyl, or —S—CH$_3$.

5. The compound of claim 1 wherein R$_5$ is fluorine.

6. The compound of claim 1, which is selected from the group consisting of:

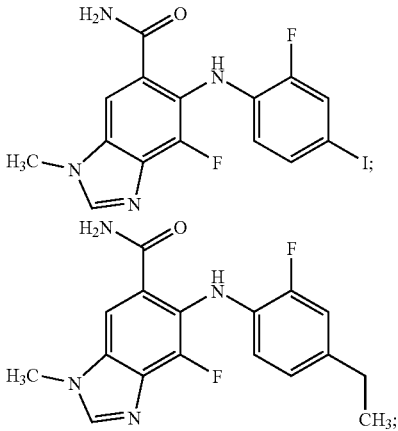

and the pharmaceutically acceptable salts thereof.

7. A method of preparing a compound or a salt of formula (I):

(I)

wherein W is —CO—Q;

Q is —NH$_2$,

R$_1$ is hydrogen, C$_{1-6}$ alkyl, C$_{2-6}$ alkenyl, C$_{2-6}$ alkynyl, C$_3$–C$_{12}$cycloalkyl, —(CR$_{10}$R$_{11}$)$_q$(C$_6$–C$_{10}$ aryl), or —(CR$_{10}$R$_{11}$)$_q$(4–10 membered heterocyclic); wherein said R$_1$ is optionally substituted with 1 to 3 substituents selected from the group consisting of —COOH, —COOR$_{14}$, —COR$_9$, —(CR$_{10}$R$_{11}$)$_q$(C$_6$–C$_{10}$ aryl), —(CR$_{10}$R$_{11}$)$_q$(4–10 membered heterocyclic), —SO$_2$R$_{11}$, —SO$_2$NR$_{12}$R$_{13}$, —OH, —OR$_{14}$, cyano, halo, —NR$_9$R$_{9a}$, and —NR$_9$CO(R$_{11}$);

R$_2$ is hydrogen, chlorine, fluorine or methyl;

R$_3$ is C$_{1-6}$ alkyl;

R$_4$ is bromine, chlorine, fluorine, iodine, C$_{1-6}$ alkyl, C$_{2-4}$ alkenyl, C$_{2-6}$ alkynyl, C$_{3-6}$ cycloalkyl, —(CH$_2$)—C$_{3-6}$cycloalkyl, cyano, —O—(C$_{1-4}$ alkyl), —S—(C$_{1-2}$ alkyl), —SOCH$_3$, —SO$_2$CH$_3$, —SO$_2$NR$_6$R$_7$, —C≡C—(CH$_2$)$_n$NH$_2$, —C≡C—(CH$_2$)$_n$NHCH$_3$, —C≡C—(CH$_2$)$_n$N(CH$_3$)$_2$, —C≡C—CH$_2$OCH$_3$, —C=C(CH$_2$)$_n$OH, —C=C—(CH$_2$)$_n$NH$_2$, —CHCHCH$_2$OCH$_3$, —CHCH—(CH$_2$)$_n$NHCH$_3$, —CHCH—(CH$_2$)$_n$N(CH$_3$)$_2$, —(CH$_2$)$_p$CO$_2$R$_6$, —C(O)C$_{1-3}$ alkyl, C(O)NHCH$_3$, —(CH$_2$)$_m$NH$_2$, —(CH$_2$)$_m$NHCH$_3$, —(CH$_2$)$_m$N(CH$_3$)$_2$, —(CH$_2$)$_m$OR$_6$, —CH$_2$S(CH$_2$)$_t$(CH$_3$), —(CH$_2$)$_p$CF$_3$, —C≡CCF$_3$, —CH=CHCF$_3$, —CH$_2$CHCF$_2$, —CH=CF$_2$, —$(CF_2)_v CF_3$, —$CH_2(CF_2)_n CF_3$, —$(CH_2)_t CF(CF_3)_2$, —$CH(CF_3)_2$, —$CF_2CF(CF_3)_2$, or —$C(CF_3)_3$, wherein the $C_{1-6}$ alkyl and $C_{2-6}$ alkynyl are optionally substituted with 1 to 3 substituents independently selected from —OH and $C_{1-6}$ alkyl;

$R_5$ is hydrogen or fluorine;

$R_6$ and $R_7$ are each independently hydrogen, methyl, or ethyl;

$R_9$ and $R_{9a}$ are each independently hydrogen or $C_{1-6}$ alkyl;

each $R_{10}$, $R_{11}$, $R_{12}$, and $R_{13}$ are $C_{1-6}$ alkyl or $C_{1-6}$ alkoxy;

$R_{14}$ is $C_{1-6}$ alkyl optionally optionally substituted with 1 to 3 substituents selected from the group consisting of —$(CR_{10}R_{11})_q(C_6$–$C_{10}$ aryl), —$(CR_{10}R_{11})_q$(4–10 membered heterocyclic);

m is 1 to 4;

n is 1 to 2;

p is 0 to 2;

t is 0 to 1;

v is 1 to 5;

q is 0 to 5;

comprising the step of:

(a) treating a compound of formula (II):

(II)

wherein $R_1$, $R_2$, $R_4$, and $R_5$ are as described above; with a compound of formula (III):

Q—H    (III);

wherein Q is as described above; in a solvent, to form said compound of formula (I).

8. The method according to claim 7, a method further comprising the step of preparing said compound of formula (II); comprising:

(b) treating a compound of formula (IV):

(IV)

wherein $R_1$, $R_2$, $R_4$, and $R_5$ are as described above; with a compound of formula $C_6F_5OH$ in the presence of a coupling agent in a solvent.

9. The method according to claim 8, wherein the coupling agent is DCC.

10. The method according to claim 8, a further comprising the step of preparing said compound of formula (IV); comprising:

(c) treating a compound of formula (V):

(V)

wherein $R_1$, $R_2$, $R_3$, $R_4$, and $R_5$ are as described above; and $R_{15}$ is —O—$R_3$, with a hydrolyzing agent in a solvent.

11. The method according to claim 10, wherein the hydrolizing agent is potassium trimethyl silanote.

12. The method according to claim 10, wherein in the compound of formula (V), $R_3$ is methyl.

13. The method according to claim 10, further comprising the step of preparing a compound of formula (V); comprising:

(d) treating a compound of formula (VI):

(VI)

wherein $R_1$, $R_2$, $R_4$, and $R_5$ are as described above;

$R_8$ is selected from the group consisting of $C_{1-6}$ alkyl, $C_{2-6}$ alkenyl, $C_{2-6}$ alkynyl, $C_3$–$C_{12}$cycloalkyl, —$(CR_{10}R_{11})_q$ $(C_6$–$C_{10}$ aryl), —$(CR_{10}R_{11})_q$(4–10 membered heterocyclic) and —$OSiR_{11}R_{12}R_{13}$; wherein said $R_8$ is optionally substituted with 1 to 3 substituents selected from the group consisting of —$(CR_{10}R_{11})_q(C_6$–$C_{10}$ aryl), —$(CR_{10}R_{11})_q$(4–10 membered heterocyclic), —$SO_2R_{11}$, —$SO_2NR_{12}R_{13}$—OH, —$OR_{14}$, cyano, —$SiR_{11}R_{12}R_{13}$, halo, —$NH_2$, and —$NHCO(R_{11})$; Lg is a leaving group selected from the group consisting of halo, sulfate esters, sulfonate esters, tetrafluoroborate and hexafluorophosphate;

each q is 0 to 5;

each $R_{10}$, $R_{11}$, $R_{12}$, and $R_{13}$ are $C_{1-6}$ alkyl or $C_{1-6}$ alkoxy;

$R_{14}$ is $C_{1-6}$ alkyl optionally optionally substituted with 1 to 3 substituents selected from the group consisting of —$(CR_{10}R_{11})_q(C_6$–$C_{10}$ aryl), —$(CR_{10}R_{11})_q$(4–10 membered heterocyclic);

$R_{15}$ is as described above;

with a deprotecting agent in a solvent.

14. The method according to claim 10, wherein $R_8$ is allyl or 4-methoxybenzyl.

15. The method according to claim 10, wherein $R_8$ is —$OSiR_{11}R_{12}R_{13}$.

16. The method according to claim 10, wherein Lg is triflate, mesylate, tosylate, tetrafluoroborate or hexafluorophosphate.

17. The method according to claim 10, wherein in said compound of formula (VI), wherein $R_3$ is methyl.

18. The method according to claim 10, further comprising the step of preparing a compound of formula (VI); comprising:

(e) treating a compound of formula (VII):

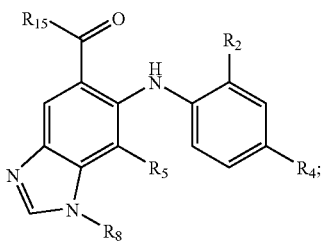

(VII)

wherein $R_2$, $R_4$, $R_5$, $R_8$, and $R_{15}$ are as described above; with a suitable alkylating agent; in a solvent.

19. The method according to claim 18, wherein said suitable alkylating agent is $C_{1-6}$alkyl tosylate or $C_{1-6}$alkyl triflate.

20. The method according to claim 18, wherein said suitable alkylating agent is $C_{1-6}$alkyl halide.

21. The method according to claim 18, wherein said suitable alkylating agent is trimethyloxonium tetrafluoroborate.

22. The method according to claim 18, wherein in said compound of formula (VII), $R_3$ is methyl.

23. The method according to claim 18, further comprising the step of preparing a compound of formula (VII); comprising:

(f) treating a compound of formula (VIII):

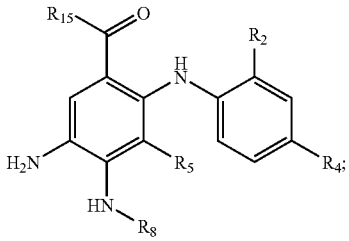

(VIII)

wherein $R_2$, $R_4$, $R_5$, $R_8$, and $R_{15}$ are as described above; with a cyclocondensation agent; in a solvent.

24. The method according to claim 23, wherein said cyclocondensation agents comprise formic acid, trimethylorthoformate, formamidine acetate, or ethyl formate.

25. The method according to claim 23, wherein in said compound of formula (VIII), $R_3$ is methyl.

26. The method according to claim 23, further comprising the step of preparing a compound of formula (VIII); comprising:

(g) treating a compound of formula (IX):

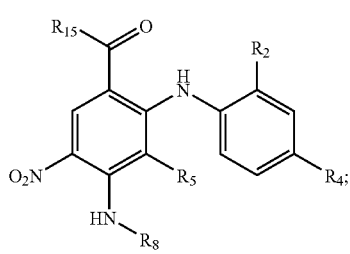

(IX)

wherein $R_2$, $R_4$, $R_5$, $R_8$, and $R_{15}$ are as described above; with a reducing agent; in a solvent.

27. The method according to claim 26, wherein in said compound of formula (IX), $R_3$ is methyl.

28. The method according to claim 26, further comprising the step of preparing a compound of formula (IX); comprising:

(h) treating a compound of formula (X):

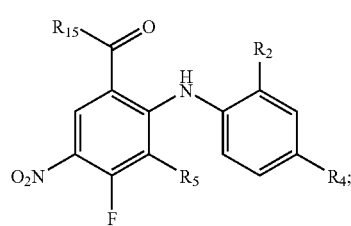

(X)

wherein $R_2$, $R_4$, $R_5$, and $R_{15}$ are as described above; with a compound of formula $R_8$—$NH_2$, wherein $R_8$ is as described above; in a solvent.

29. The method according to claim 26, wherein said compound of formula $R_8$—$NH_2$ is 2-hydroxyethylamine or 4-methoxybenzylamine.

30. The method according to claim 26, wherein in said compound of formula (X), $R_3$ is methyl.

31. The method according to claim 26, further comprising the step of preparing a compound of formula (X); comprising:

(i) treating a compound of formula (XI):

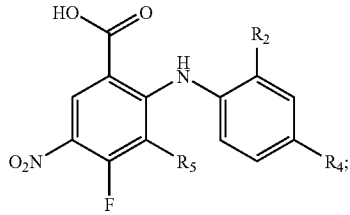

(XI)

wherein $R_2$, $R_4$, and $R_5$ are as described above; with a suitable amidating agent; in a solvent.

32. The method according to claim 31, wherein the suitable amidating agent comprises a combination of a halogenating agent and a suitable amine.

33. The method according to claim 31, further comprising the step of preparing a compound of formula (XI); comprising:

(j) treating a compound of formula (XII):

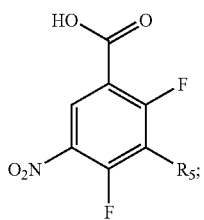
(XII)

wherein $R_5$ is as described above;
with a compound of formula (XIII):

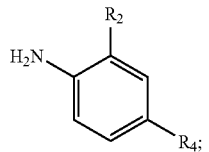
(XIII)

wherein $R_2$ and $R_4$ are as described above; in the presence of a strong base in a solvent.

34. The method according to claim 33, further comprising the step of preparing a compound of formula (XII); comprising:
(k) treating a compound of formula (XIV):

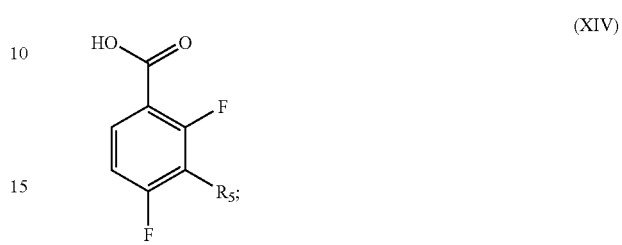
(XIV)

wherein $R_5$ is as described above;
with a nitro-producing agent in a solvent.

35. The method according to claim 34, wherein the nitro-producing agent is $HCl/H_2SO_4$.

36. A pharmaceutical composition comprising a compound of claim 1 and a pharmaceutically acceptable carrier.

* * * * *